(12) United States Patent
Hiroi et al.

(10) Patent No.: US 7,266,235 B2
(45) Date of Patent: *Sep. 4, 2007

(54) PATTERN INSPECTION METHOD AND APPARATUS

(75) Inventors: Takashi Hiroi, Yokohama (JP); Masahiro Watanabe, Yokohama (JP); Chie Shishido, Yokohama (JP); Aritoshi Sugimoto, Tokyo (JP); Maki Tanaka, Yokohama (JP); Hiroshi Miyai, Hitachi (JP); Asahiro Kuni, Tokyo (JP); Yasuhiko Nara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 491 days.

This patent is subject to a terminal disclaimer.

(21) Appl. No.: 09/986,577

(22) Filed: Nov. 9, 2001

(65) Prior Publication Data

US 2002/0057831 A1 May 16, 2002

Related U.S. Application Data

(62) Division of application No. 09/986,299, filed on Nov. 8, 2001, now Pat. No. 7,133,550.

(30) Foreign Application Priority Data

Nov. 9, 2000 (JP) .............................. 2000-347443

(51) Int. Cl.
*G60K 9/00* (2006.01)

(52) U.S. Cl. ...................... 382/145; 382/147; 382/149; 382/141; 348/87; 348/126; 356/237.1

(58) Field of Classification Search ................ 382/145, 382/147, 149, 141; 348/86, 87, 125, 126, 348/130; 356/237.1, 237.2, 237.5, 904, 239.3; 250/306, 307, 311, 559.05, 559.06, 559.07, 250/559.39, 492.1, 492.2; 700/110, 121; 438/14, 16

See application file for complete search history.

(56) References Cited

U.S. PATENT DOCUMENTS 4,247,203 A * 1/1981 Levy et al. ................. 356/398

(Continued)

FOREIGN PATENT DOCUMENTS

JP 61-278706 12/1986

(Continued)

*Primary Examiner*—Bhavesh M Mehta
*Assistant Examiner*—John Strege
(74) *Attorney, Agent, or Firm*—Antonelli, Terry, Stout & Kraus, LLP.

(57) ABSTRACT

A pattern inspection method in which an image can be detected without an image detection error caused by an adverse effect to be given by such factors as ions implanted in a wafer, pattern connection/non-connection, and pattern edge formation. A digital image of an object substrate is attained through microscopic observation thereof, the attained digital image is examined to detect defects, while masking a region pre-registered in terms of coordinates, or while masking a pattern meeting a pre-registered pattern, and an image of each of the defects thus detected is displayed. Further, each of the defects detected using the digital image attained through microscopic observation is checked to determine whether its feature meets a pre-registered feature or not. Defects having a feature that meets the pre-registered feature are so displayed that they can be turned on/off, or they are so displayed as to be distinguishable from the other defects.

13 Claims, 16 Drawing Sheets

U.S. PATENT DOCUMENTS

| | | | |
|---|---|---|---|
| 4,989,156 A | | 1/1991 | Ikenaga |
| 5,321,767 A | * | 6/1994 | Murase ........................ 382/149 |
| 5,850,467 A | | 12/1998 | Matsui et al. |
| 6,246,787 B1 | * | 6/2001 | Hennessey et al. .......... 382/141 |
| 6,259,960 B1 | * | 7/2001 | Inokuchi ...................... 700/110 |
| 6,539,106 B1 | * | 3/2003 | Gallarda et al. ............. 382/149 |
| 6,763,130 B1 | * | 7/2004 | Somekh et al. .............. 382/145 |

FOREIGN PATENT DOCUMENTS

| | | |
|---|---|---|
| JP | 02-146682 | 6/1990 |
| JP | 03-085742 | 4/1991 |
| JP | 05-258703 | 10/1993 |
| JP | 07-005116 | 1/1995 |
| JP | 09-312318 | 12/1997 |
| JP | 11-160247 | 6/1999 |

* cited by examiner

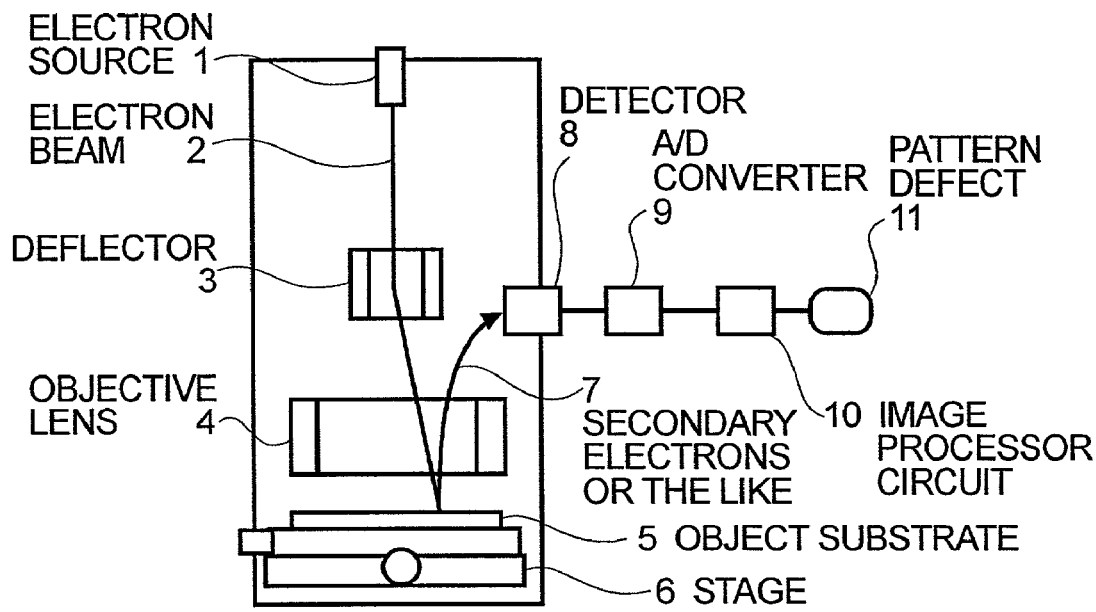
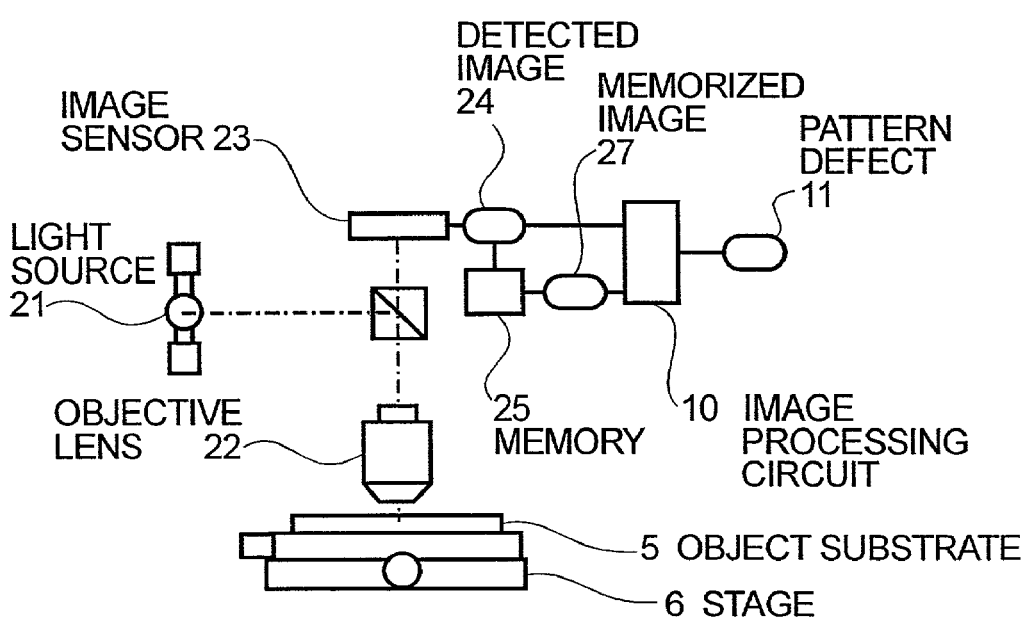

31
WAFER ated analog signal is output from the detector 8. Then, through an A/D converter 9, the detected analog signal is converted into a digital image. In an image processor circuit 10, the digital image thus produced is compared with a reference digital image which is expected to be identical thereto. If any difference is found, the difference is judged to be a pattern defect 11, and the location thereof is determined.

PATTERN INSPECTION METHOD AND APPARATUS

BACKGROUND OF THE INVENTION

This is a divisional application of application Ser. No. 09/986,299, filed Nov. 8, 2001 now U.S. Pat. No. 7,133,550.

The present invention relates to a method and apparatus for fabricating substrates having circuit patterns, such as semiconductor devices and liquid crystal display devices, and, more particularly, to a technique for inspecting substrate patterns in a fabrication process.

Conventional optical or electron-beam pattern inspection apparatuses have been proposed in JP-A Nos. H5(1993)-258703, H11(1999)-160247, S61(1986)-278706, H7(1995)-5116, H2(1990)-146682, H9(1997)-312318, and H3 (1991)-85742, for example.

FIG. 1 shows an example of an electron-beam pattern inspection apparatus of the type disclosed in JP-A No. H5(1993)-258703. In this conventional electron-beam pattern inspection apparatus, an electron beam 2 emitted from an electron source 1 is deflected in the X direction by a deflector 3, and the electron beam 2 thus deflected impinges on an object substrate 5 under test after passing through an objective lens 4. Simultaneously, while a stage 6 is moved continuously in the Y direction, secondary electrons 7 or the like produced from the object substrate 5 are detected by a detector 8. Thus, a detected analog signal is output from the detector 8. Then, through an A/D converter 9, the detected analog signal is converted into a digital image. In an image processor circuit 10, the digital image thus produced is compared with a reference digital image which is expected to be identical thereto. If any difference is found, the difference is judged to be a pattern defect 11, and the location thereof is determined.

FIG. 2 shows an example of an optical pattern inspection apparatus of the type in JP-A No. H11 (1999)-160247. In this conventional optical inspection apparatus, a light beam emitted from a light source 21 is applied to an object substrate 5 under test through an objective lens 22, and light reflected from the object substrate 5 is detected by an image sensor 23. While a stage 6 is moved at a constant speed, detection of reflected light is repeated to produce a detected image 24. The detected image 24 thus produced is stored into a memory 25. In an image processing circuit 10, the detected image 24 is compared with a previously memorized reference image 27, which is expected to have a pattern identical to that of the detected image 24. If the pattern of the detected image is identical to that of the reference image 27, it is judged that there is no defect, on the object substrate 5. If these patterns are not identical to each other, a pattern defect 11 is recognized, and the location thereof is determined.

As an example, FIG. 3 shows a layout of a wafer 31 corresponding to the object substrate 5. On the wafer 31, there are formed dies 32 which are to be separated eventually as individual identical products. The stage 6 is moved along a scanning line 33 to detect images in a stripe region 34. In a situation where a detection position A 35 is currently taken, a pattern image attained at the detection position A 35 is compared with a pattern image attained at a detection position B 36 (reference pattern image 27), which has been stored in the memory 25. Thus, each pattern image is compared with a reference pattern image which is expected to be identical thereto. In this arrangement, the memory 25 has a storage capacity sufficient for retaining reference pattern image data to be used for comparison, and the circuit structure of the memory 25 is designed to perform a circular-shift memory operation.

In the following two examples, a defect check is conducted using a binary image of an object under test. In synchronization with pattern detection, a judgment is formed on whether a pattern of the object is defective or not while ignoring a possible defect in a particular mask region.

In JP-A No. S61(1986)-278706, there is disclosed an example of a technique for inspecting through-holes on a printed circuit board. In this inspection technique, a printed circuit board having through-holes only in a non-inspection region thereof is prepared beforehand, and an image of the printed circuit board is taken prior to inspection. A binary image indicating the presence/absence of through-holes is thus attained for masking, and it is stored as image data in a masking data storage. At the time of inspection, if a difference found in binary image comparison is located at a position included in a mask region stored in the masking data storage, the difference is ignored for non-inspection.

In JP-A No. H7(1995)-5116, there is disclosed an example of a technique for printed circuit board inspection. In this inspection technique, a pattern is detected to provide binary image data, and using the binary image data, a judgment is formed on whether the detected pattern is normal or not; more specifically, it is checked to determine whether the detected pattern meets any specified regular pattern or not. If not, the detected pattern is judged to be defective.

In the following two examples, using pattern data, a dead zone is provided for the purpose of allowing an error at a pattern boundary in inspection.

In JP-A No. H2(1990)-146682, there is disclosed an example of an inspection technique in which a mask pattern is compared with design data. Through calculation of design data, a pattern is reduced by a predetermined width to attain a reduced image, and also the pattern, is enlarged by a predetermined width to attain an enlarged image. Then, a part common to the reduced image and the enlarged image is extracted to provide a dead zone having a certain width. Thus, using the design data, a mask region is provided so that an error at a pattern boundary having a certain width will be ignored during inspection.

In JP-A No. H9(1997)-312318, there is disclosed an example of a technique for inspecting patterns using a scanning electron microscope (hereinafter referred to just as a "SEM"). Using a reference image acquired in advance, a vicinal area of a pattern edge is set up as a region where no critical defect occurs, since a minuscule deviation of a pattern edge is not regarded as a defect. Thus, an image of the region where no critical defect occurs is ignored. If any difference is found between the reference image and an image of a pattern under test, excluding the region where no critical defect occurs, the difference is judged to be a pattern defect.

In JP-A. No. H3(1991)-85742, there is disclosed an example of a system for carrying out comparative inspection of printed circuit patterns. An image of a candidate defect attained in comparative inspection, is stored in memory. Then, not simultaneously with the comparative inspection, the memorized image is examined to judge whether a difference is actually a defect or not.

On an object under test, there is an area where a considerable difference is found in comparative inspection of patterns, even if the difference is not actually a defect. For example, on an ion-implanted region for formation of a transistor, a non-defective difference may be found in comparative inspection of patterns. Although a difference between a part where ions have been implanted and a part where ions have not been implanted is important at a location of a transistor element, the characteristics of wiring areas, other than transistor element locations, are not affected by the presence/absence of implanted ions. Therefore, in an ion implantation process, rough masking is used to determine where ions are to be implanted. However, in electron-beam inspection of wiring areas, a considerable difference attributable to whether implanted ions are present or not may be detected, resulting in a wrong judgment indicating that the difference represents a defect.

Further, for example, in a power line layer where redundant wiring is provided, even if a part of the wiring is not connected, circuit normality can be ensured by providing a connection at another point. Therefore, in some cases, rough patterning is provided for a power wiring arrangement, so that no-connection on pattern elements are left. In comparative inspection of detected images, a difference attributable to whether a connection is provided or not nay be found, resulting in a wrong judgment indicating that the difference represents a defect.

Still further, for example, on a pattern edge, a detected signal level varies depending on the thickness/inclination of a film thereof. Although up to a certain degree of variation in detected signal output may be ignored, a considerable difference in detected signal output is likely to be taken as a defect mistakenly. A degree of false defect detection is however applicable as an index representing product quality. It is desirable to examine the degree of false defect detection and preclude false defects before carrying out defect inspection.

In the conventional optical/electron-beam pattern inspection apparatuses disclosed in JP-A Nos. H5(1993)-258703 and H11 (1999)-160247, it is not allowed to set up a non-inspection region.

In the inspection techniques disclosed in JP-A Nos. S61 (1986)-278706 and H7 (1995)-5116, there is provided a non-inspection region. However, according to an example presented in JP-A No. S61(1986)-278706, it is required to specify a non-inspection region covering a very large area by using a bit pattern. In application to wafer inspection, a wafer surface area 300 mm in diameter has to be inspected using pixels each having a size of 0.1 µm. This requires an impractically large number of pixels, i.e., seven tera-pixels (seven terabits). According to the inspection technique disclosed in JP-A No. H7 (1995)-5116, any areas other than regular pattern areas are treated as non-inspection regions. Since very complex patterns are formed on a wafer, a non-inspection region cannot be set up just by means of simple pattern regularity.

In the inspection techniques disclosed in JP-A Nos. H2 (1990)-146682 and H9 (1997)-312318, the use of a non-inspection region is limited to a pattern edge, and therefore it is not allowed to set up a non-inspection region at an arbitrary desired location.

In the inspection system disclosed in JP-A No. H3 (1991)-85742, image data of a candidate defect is stored, and then detail inspection is carried out using the stored image data to check whether a difference is actually a defect or not. This approach is applicable to inspection of complex pattern geometries. However, based on predetermined criteria, a judgment is formed on whether a difference is actually a defect or not. Any part may be judged to be normal if requirements based on predetermined criteria are satisfied. That is to say, once a part is judged to be normal, data regarding the part will be lost.

As described above, in the conventional pattern inspection techniques, it is not allowed for a user to set up a non-inspection region effective for a device having a complex, large pattern area to be inspected, such as a wafer. Further, in cases where a considerable difference is found in comparative inspection of detected images even if the difference is not actually a defect, it is likely to be misjudged that the difference represents a defect. In addition to these disadvantages, the conventional pattern inspection techniques are also unsatisfactory as regards stability in detection of minuscule defects.

SUMMARY OF THE INVENTION

It is therefore an object of the present invention to overcome the above-mentioned disadvantages of the prior art by providing a pattern inspection method and apparatus for enabling a user to easily set up a non-inspection region effective for a device having a complex, large pattern area to be inspected.

In accomplishing this object of the present invention, and according to one aspect thereof, there is provided a pattern inspection apparatus such as shown in FIG. 4. While an exemplary configuration of an electron-beam pattern inspection apparatus is presented here, an optical pattern inspection apparatus can be configured in the same fashion in principle. The electron-beam pattern inspection apparatus shown in FIG. 4 comprises an electron source 1 for emitting an electron beam 2, a deflector 3 for deflecting the electron beam 2, an objective lens 4 for converging the electron beam 2 onto an object substrate 5 under test, a stage 6 for holding the object substrate 5 and for scanning/positioning the object substrate 5, and a detector 8 for detecting secondary electrons 7 or the like produced from the object substrate 5 to output a detected analog signal. An A/D converter 9 converts the detected analog signal into a digital image, and an image processor circuit 10 compares the converted digital image with a reference digital image expected to be identical thereto and identifies a difference found in comparison as a candidate defect 40. A candidate defect memory part 41 is provided for storing feature quantity data of each candidate defect 40, such as coordinate data, projection length data and shape data, and a mask setting part 44 examines pattern defects 11 stored in the candidate defect memory part 41 and flags a candidate defect located in a mask region 42 (shown in FIG. 5), prespecified with coordinates, as a masked defect 43 (shown in FIG. 5). An operation display 45 is provided on which data of pattern defects 11 received from the mask setting part 44 is displayed, an image of a selected pattern defect 11 is displayed, and the mask region 42 is displayed or edited.

The operations in the electron-beam pattern inspection apparatus, configured as mentioned above, will be described. Referring now to FIG. 5, the mask region 42 will be described first.

On the object, substrate 5, there is an area where a considerable difference is found in comparative inspection of patterns, even if the difference is not actually a defect, such as a region 50 where ions have been implanted. In actual practice, during ion implantation, ions are likely to be implanted in a deviated fashion, i.e., a deviated ion-implanted part 52 is formed in addition to normal ion-implanted pattern parts 51. The deviated ion-implanted part 52 has no adverse effect on device characteristics, i.e., the deviated ion-implanted pan 52 should be judged to be non-defective. However, the deviated ion-implanted part 52 is detected as a pattern defect 11. Therefore, an area including the ion-implanted region 50 is set up as a mask region 42, and a possible defect in the mask region 42 is treated as a masked defect 43. Since the same die pattern is formed repetitively on the wafer 31 shown in FIG. 3, on-die coordinates are used in region recognition. Parts, having the sane coordinates on different dies are regarded as identical, and if in-die coordinates of a part are included in a specified region, it is regarded that the part is included in the specified region. For the wafer 31, beam shots are also characterized by repetitiveness besides dies. Each shot is a unit of beam exposure in a pattern exposure system used for semiconductor device fabrication. For identifying some kinds of false defects to be precluded in pattern inspection, the use of shots may be more suitable than that of dies with respect to pattern repetitiveness. Although the following description handles dies, it will be obvious to those skilled in the art that shots are applicable in lieu of dies and that an arrangement may be provided for allowing a changeover between shots and dies.

Operations in the electron-beam pattern inspection apparatus according to the present invention include a conditioning operation in which the mask region 42 is defined and an inspection operation in which any candidate defect 40 detected in other than the mask region 42 is judged to be a pattern defect.

In the conditioning operation, the mask region 42 is cleared, the electron beam 2 emitted from the electron source 1 is deflected in the X direction by the deflector 3, and the electron beam 2 thus deflected is applied to the object substrate 5 through the objective lens 4. Simultaneously, while the stage 6 is moved continuously in the Y direction, secondary electrons 7 or the like produced from the object substrate 5 are detected by the detector 8. Thus, a detected analog signal is output from the detector 8. Then, through the A/D converter 9, the detected analog signal is converted into a digital image. In the image processor circuit 10, the digital image thus produced is compared with a reference digital image which is expected to be identical thereto. If any difference is found in comparison, the difference is indicated as a candidate defect 40. Feature quantity data of each candidate defect 40, such as coordinate data, projection length data and shape data (image data), is stored into the candidate defect memory part 41. In the mask setting part 44, pattern defects 11 are set using feature quantity data of respective candidate defects 40. The pattern defects 11 are superimposed on an image of the object substrate 5, and the resultant image is presented on a map display part 55 of an operation display 45 (screen), as shown in FIG. 6. The user can select any one of the pattern defects 11 (including true defects 57 and, false defects 58 not to be detected, in FIG. 6) on the map display part 55 of the operation display 45. An image of a pattern defect 11 selected on the map display part 55 is presented on an image display part 56 of the operation display 45. By checking the image of each of the pattern defects 11 on the image display part 56, the user classifies the pattern defects 11 into true defects 57 and false defects 58 not to be detected. The results of this classification are indicated as particular symbols on the map display part 55.

After completion of the defect classification mentioned above, the user selects an operation display screen shown in FIG. 7, which comprises a map display part 55 for presenting an enlarged map including true defects 57, false defects 58 not to be detected and a current position indicator 59, and an image display part 56 for presenting an image corresponding to the current position indicator 59. On the map display part 55, the user can specify a mask region 42 and check a position of each pattern defect 11. With reference to classification information on each pattern defect 11 and the image corresponding to the current position indicator 59, the user sets up coordinates of a mask region 42 so that the false defects 58 will not be detected. As required, the user carries out the conditioning operation again to set up the coordinates of the mask region 42 more accurately.

In the inspection operation, the electron beam 2 emitted from the electron source 1 is deflected in the X direction by the deflector 3, and the electron beam 2 thus deflected is applied to the object substrate 5 through the objective lens 4. Simultaneously, while the stage 6 is moved continuously in the Y direction, secondary electrons 7 or the like produced from the object substrate 5 are detected by the detector 8. Thus, a detected analog signal is output from the detector 8. Then, through the A/D converter 9, the detected analog signal is converted into a digital image. In the image processor circuit 10, the digital image thus produced is compared with a reference digital image which is expected to be identical thereto. If any difference is found in comparison, the difference is indicated as a candidate defect 40. Feature quantity data of each candidate defect 40, such as coordinate data, projection length data and shape data (image data), is stored into the candidate defect memory part 41. The feature quantity data of each candidate defect 40 is examined to judge whether the candidate defect 40 is located in the specified mask region 42 or not. If it is determined that the candidate defect 40 is not located in the specified mask region 42, the candidate defect 40 is defined as a pattern defect 11. Then, the pattern defect 11 is superimposed on an image of the object substrate 5, and the resultant image is presented on the map display part 55. Even if the candidate defect 40 is not defined as a pattern defect 11, the feature quantity data thereof is retained so that it can be displayed again. This makes it possible for the user to avoid forming a wrong judgment that a considerable non-defective difference is a defect.

In the above-mentioned arrangement of the present invention, the mask setting part 44 is used for determining a false defect not to be detected. While coordinates are used in the mask setting part 44 as exemplified above, any other pattern data or feature quantity data of each candidate defect image is also applicable for identification. On a pattern edge, a degree of variation in detected signal out put dues not depend on, coordinates, and therefore pattern-edge feature quantity data is used for identification instead of coordinate data.

Further, while masking is made for non-inspection of candidate defects, as exemplified above, another inspection means, or a method of inspection based on another criterion is also applicable to examination of an area corresponding to a mask region. In this case, according to conditions specified by the user after inspection, a defect judgment can be formed again regarding candidate defects 40 stored in the candidate defect memory part 41.

As described above, and according to the present invention, the user can set up a non-inspection region which is effective for a device having a complex, large pattern area to be inspected, such as a wafer. Further, in cases where a considerable difference is found in comparative inspection of detected images, even if the difference is not actually a defect, the present invention makes it possible to avoid false defect detection while carrying out detection of minuscule defects.

These and other objects, features and advantages of the invention will be apparent from the following mere particular description of preferred embodiments of the invention, as illustrated in the accompanying drawings.

BRIEF DESCRIPTION OF THE DRAWINGS

FIG. 1 is a schematic diagram of a conventional electron-beam pattern inspection apparatus;

FIG. 2 is a schematic diagram of a conventional optical pattern inspection apparatus;

DETAILED DESCRIPTION OF THE PREFERRED EMBODIMENTS

The present invention will now be described in detail by way of example with reference to the accompanying drawings.

Embodiment 1

Figure 8:
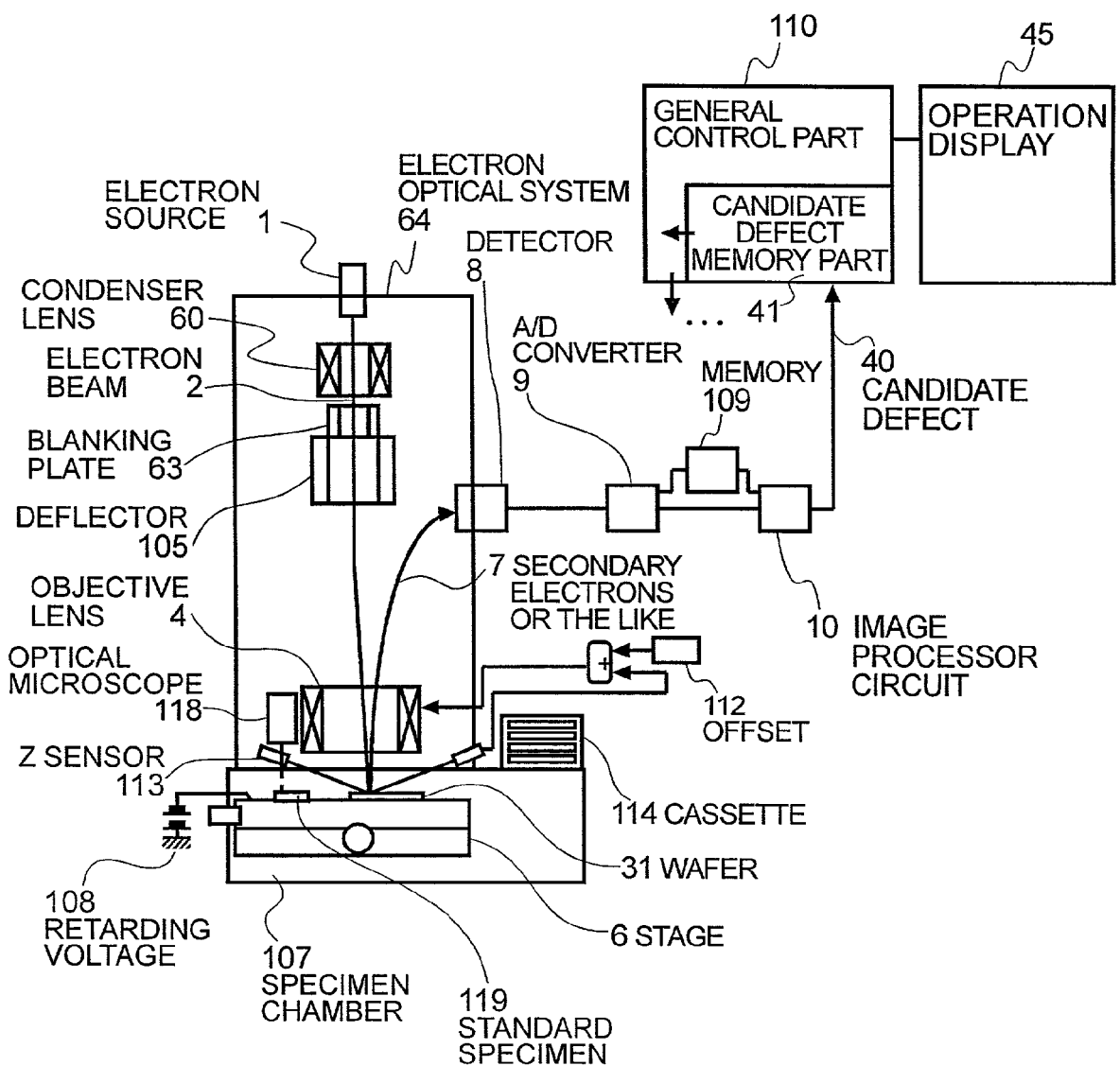
FIG. 8 is a schematic diagram showing the configuration of an electron-beam pattern inspection apparatus in a first preferred embodiment of the present invention.

A first preferred embodiment of the present invention will be described. FIG. 8 shows the configuration of an electron-beam pattern inspection apparatus according to the first preferred embodiment of the present invention. The electron-beam pattern inspection apparatus comprises an electron optical system 106, including: an electron source 1 for emitting an electron beam 2 from an electron gun in which the electron beam 2 from the electron source 1 is extracted and accelerated by an electrode to produce a virtual electron source at a predetermined point through an electrostatic or magnetic field superimposing lens; a condenser lens 60 for converging the electron beam 2 from the virtual electron source at a predetermined convergence point; a blanking plate 63 which is equipped in the vicinity of the convergence point of the electron beam 2 for turning on/off the electron beam 2; a deflector 105 for deflecting the electron beam 2 in the X and Y directions; and an objective lens 4 for converging the electron beam 2 onto an object substrate (wafer 31).

Figure 5:
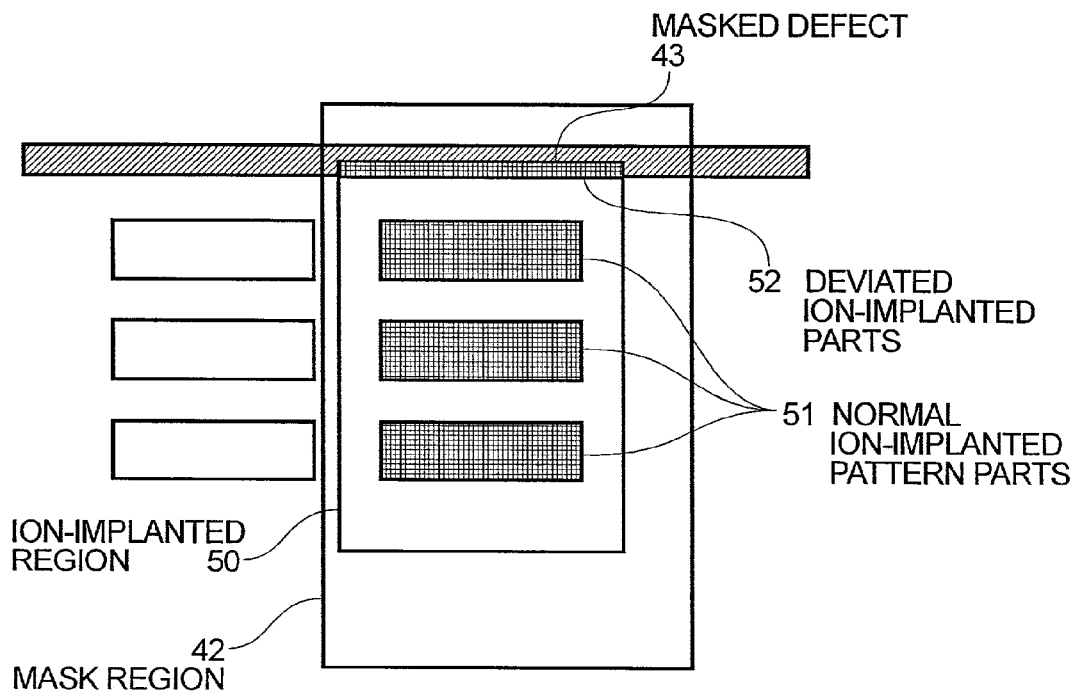
FIG. 5 is a diagrammatic plan view illustrating operation of the first problem-solving means according to the present invention.
Figure 6:
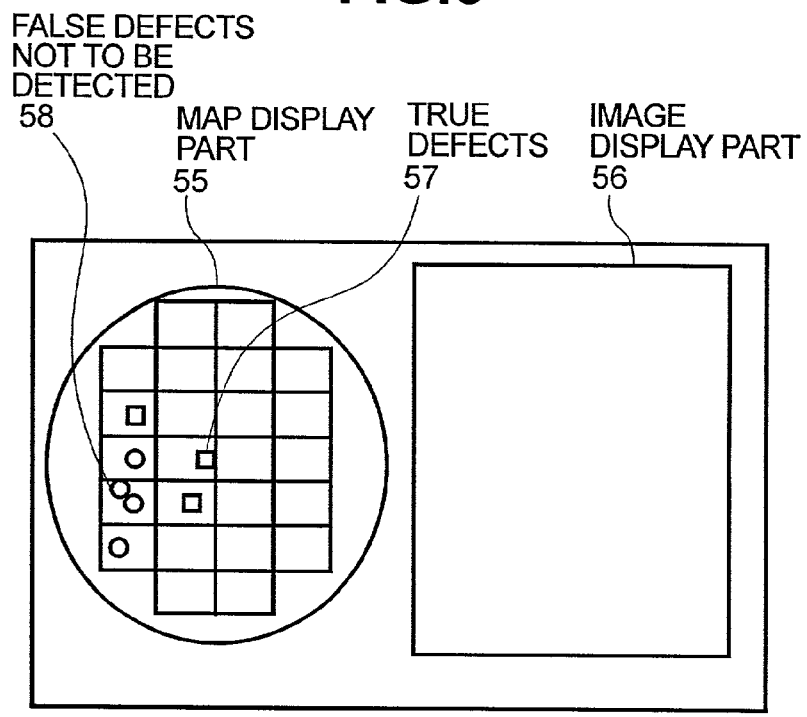
FIG. 6 is a diagram showing the layout of a defect check screen.
Figure 7:
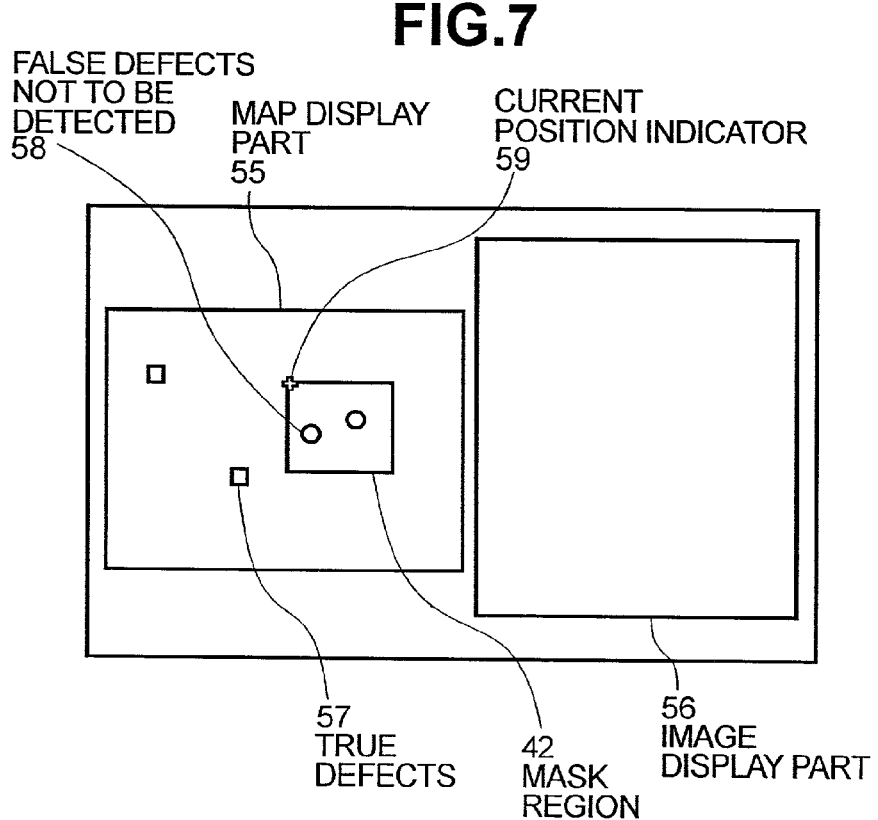
FIG. 7 is a diagram showing the layout of a mask region setting screen.

Further, the electron-beam pattern inspection apparatus comprises a specimen chamber 107 in which the object substrate (wafer 31) is held in a vacuum; a stage 6 where the wafer 31 is mounted and to which a retarding voltage 108 is applied for enabling detection of an image at an arbitrary position; and a detector 8 for detecting secondary electrons 7 or the like produced from the object substrate to output a detected analog signal. An A/D converter 9 is provided for converting the detected analog signal into a digital image, which is stored in a memory 109 for storing digital image data, and an image processor circuit 10 compares the converted digital image with a reference digital image stored in the memory 109 and identifies a difference found in comparison as a candidate defect 40. A candidate defect memory part 41, which stores feature quantity data of each candidate defect 40, such as coordinate data, projection length data and shape data, is provided in a general control part 110, in which the overall apparatus control is conducted, with feature quantity data of each pattern defect 11 being received from the candidate defect memory part 41. A mask region 42 (shown in FIG. 5) is set as region data, and a candidate defect located in the mask region 42 is flagged as a masked defect 43 (shown. in FIG. 5) (control lines from the general control part 110 are not shown in FIG. 8). An operation display 45 is provided on which data of pattern defects 11 is displayed, an image of a selected pattern defect 11 is displayed, and the mask region 42 is displayed or edited.

Still further, the electron-beam pattern inspection apparatus comprises a keyboard, a mouse and a knob (not shown) for operation and control; a Z sensor for measuring the height level of each wafer 31 to maintain a focal point of a detected digital image through control of a current applied to the objective lens by adding an offset 112; a loader (not shown) for loading the wafer 31 from its cassette 114 to the specimen chamber 107 and for unloading the wafer 31 from the specimen chamber 107 to the cassette 114; an orientation flat detector (not shown) for positioning the wafer 31 according to the circumferential shape of the wafer 31; an optical microscope 118 for allowing observation of a pattern on the wafer 31; and a standard specimen 119, which is set on the stage 6.

Operations in the first preferred embodiment include a conditioning operation, in which a mask region 42 is set up, and an inspection operation, in which any candidate defect 40 detected in other than the mask region 42 is examined as a pattern defect.

Figure 9:
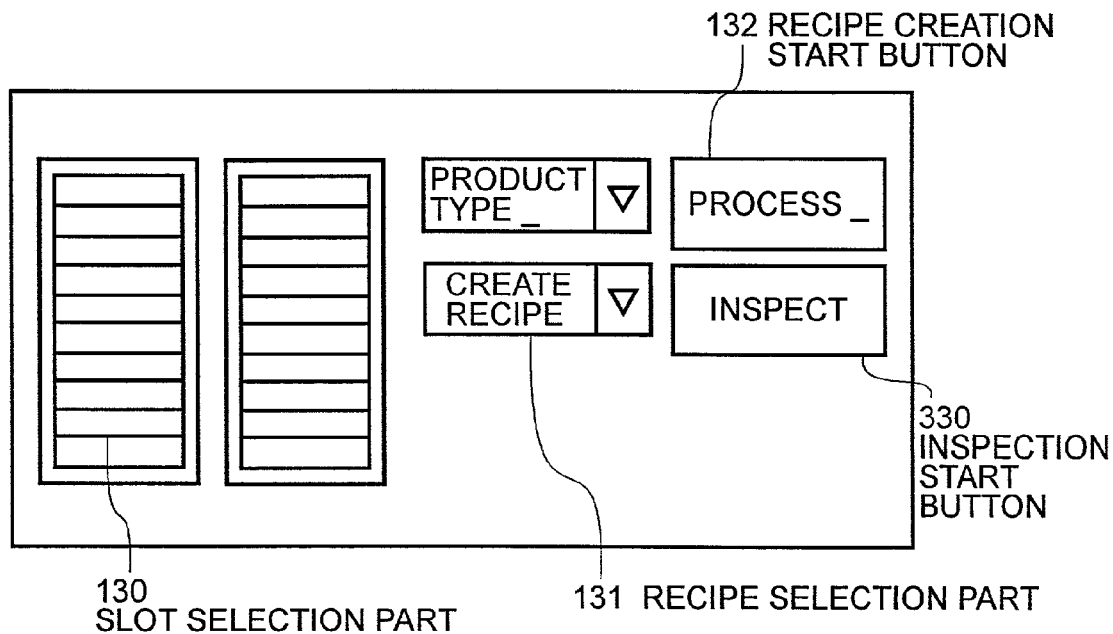
FIG. 9 is a diagram showing a startup screen in the first preferred embodiment of the present invention.

In the conditioning operation, a user opens a startup screen shown in FIG. 9 on the operation display 45. On a slot selection part 130 of the startup screen, the user selects a code number of a slot where the wafer 31 to be inspected is contained. Then, on a recipe selection part 131, the user specifies a product type of the wafer 31 and a process step thereof, and the user presses a recipe creation start button 132 for starting the conditioning operation. The conditioning operation includes contrast setting for the electron optical system, pattern layout setting for the wafer 31, pattern positioning alignment for the wafer 31, calibration in which a signal level of the wafer 31 is checked at a position where the signal level is indicated accurately, inspection condition setting, mask region setting, and a setup condition check in trial inspection. The contrast setting, mask region setting, and trial inspection, which form essential parts of the present invention, will be described.

The general control part 110 provides operational instructions to each part in the following manner.

First, the general control part 110 issues an operational instruction to the loader (not shown) so that the loader takes the wafer 31 out of the cassette 114. Then, through the use of the orientation flat detector (not shown), the circumferential shape of the wafer 31 is checked, and the wafer 31 is positioned according to the result of this check. The wafer 31 is then mounted on the stage 6, and the specimen chamber 107 is evacuated. Simultaneously, the electron optical system and the retarding voltage 108 are conditioned. A voltage is applied to the blanking plate 63 to turn off the electron beam 2. The stage 6 is moved so that the standard specimen 119 can be imaged, and an output of the Z sensor 113 is made effective. While a focal point of the electron beam 2 from the electron optical system is maintained at a position corresponding to "a value detected by the Z sensor 113+an offset 112", raster scanning is performed by the deflector 105. In synchronization with this raster scanning, the voltage applied to the blanking plate 63 is turned off so that the wafer 31 is irradiated with the electron beam 2 as required. Backscattered electrons or secondary electrons produced from the wafer 31 are detected by the detector 8, which then outputs a detected analog signal. Through the A/D converter 9, the detected analog signal is converted into a digital image. By changing the offset 112, a plurality of digital images are detected, and in the general control part 110, an optimum offset for maximizing the sun of image differential values is determined. The optimum offset thus determined is set up as the current offset value.

Figure 10:
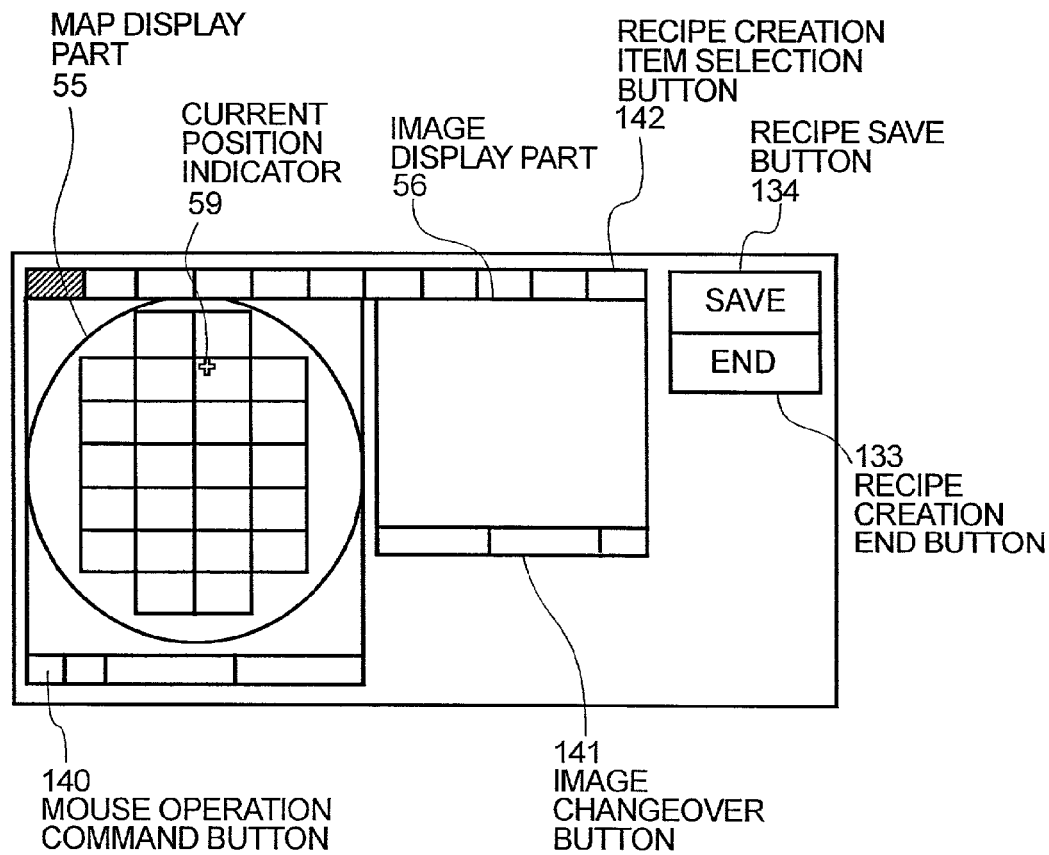
FIG. 10 is a diagram showing a contrast adjustment screen for recipe creation in the first preferred embodiment of the present invention.

After the optimum off set is established, the output of the Z sensor 113 is made ineffective, and a screen transition is made to the contrast adjustment screen shown in FIG. 10. The contrast adjustment screen comprises: a map display part 55 having a map display area, a button for controlling display of the entire wafer or die map, and a mouse operation command button 140 for controlling position movement or item selection by the use of the mouse (not shown); an image display part 56, having an image display area and an image changeover button 141 for setting an image magnification, for selecting an optical micrograph image attained through the optical microscope 118 or a SEM image attained through the electron optical system, and for specifying a kind of image; a recipe creation item selection button 142; a recipe creation end button 133; and a recipe save button 134. On the contrast adjustment screen, the user sets the mouse operation command button 140 to a movement mode, and performs movement on the map by clicking the mouse to view an image at the current position on the image display part. Then, the user assigns an adjustment item of the electron optical system to the knob, and adjusts each part of the electron optical system to attain proper contrast.

Figure 11:
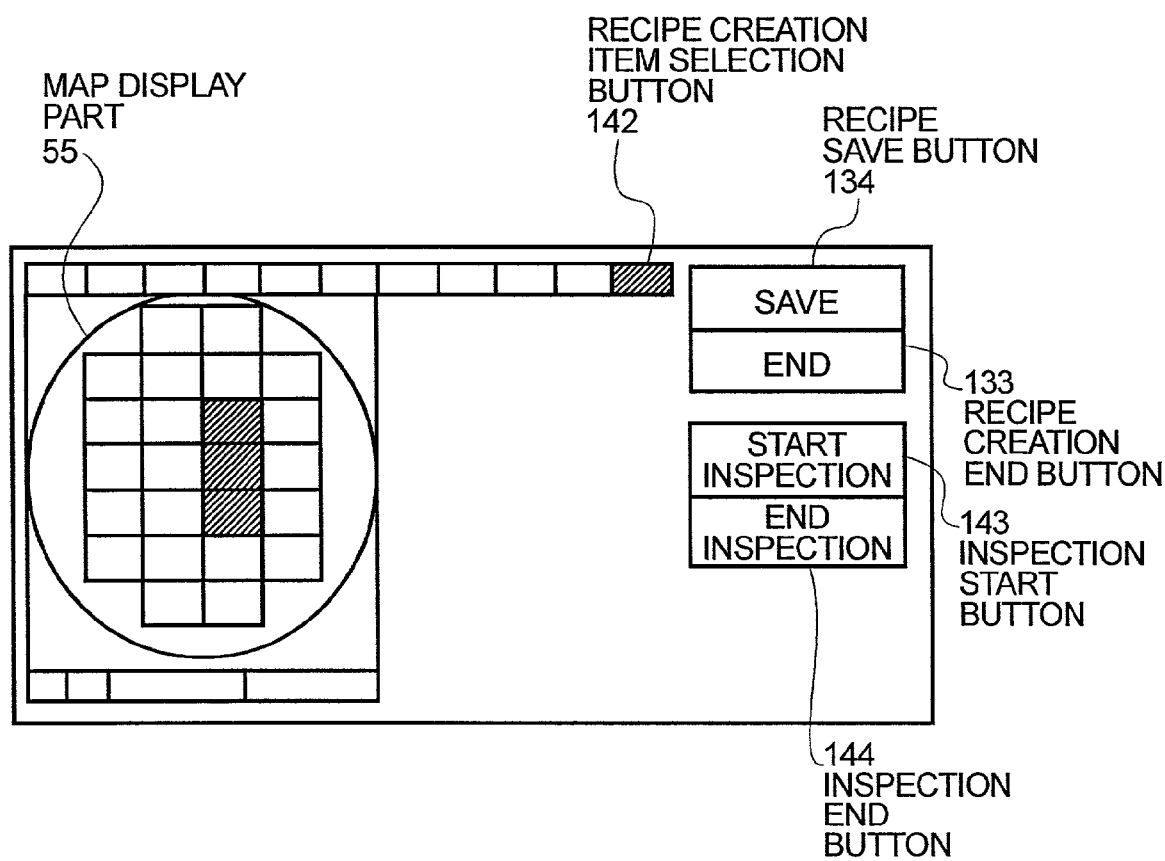
FIG. 11 is a diagram showing a trial inspection initial screen for recipe creation in the first preferred embodiment of the present invention.

The recipe creation end button 133 is used for terminating recipe creation; the recipe save button 134 is used for saving recipe condition data; and the recipe creation item selection button 142 is used for setting another condition and issuing an instruction for screen transition. These buttons are available on all of the screens. To open a trial inspection initial screen, as shown in FIG. 11, the user sets the recipe creation item selection button 142 to a trial inspection item.

Figure 3:
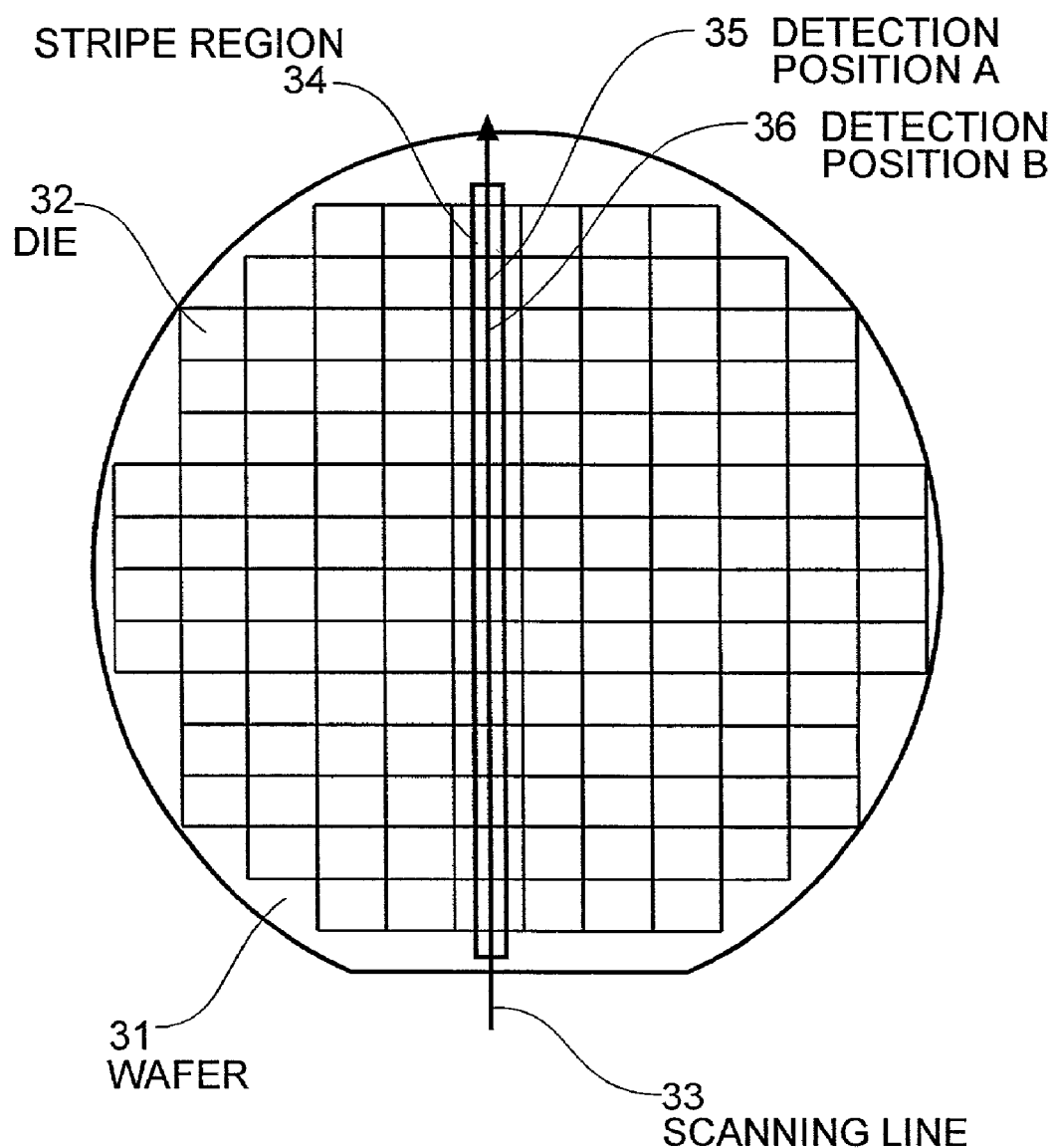
FIG. 3 is a plan view showing a layout of a wafer.
Figure 4:
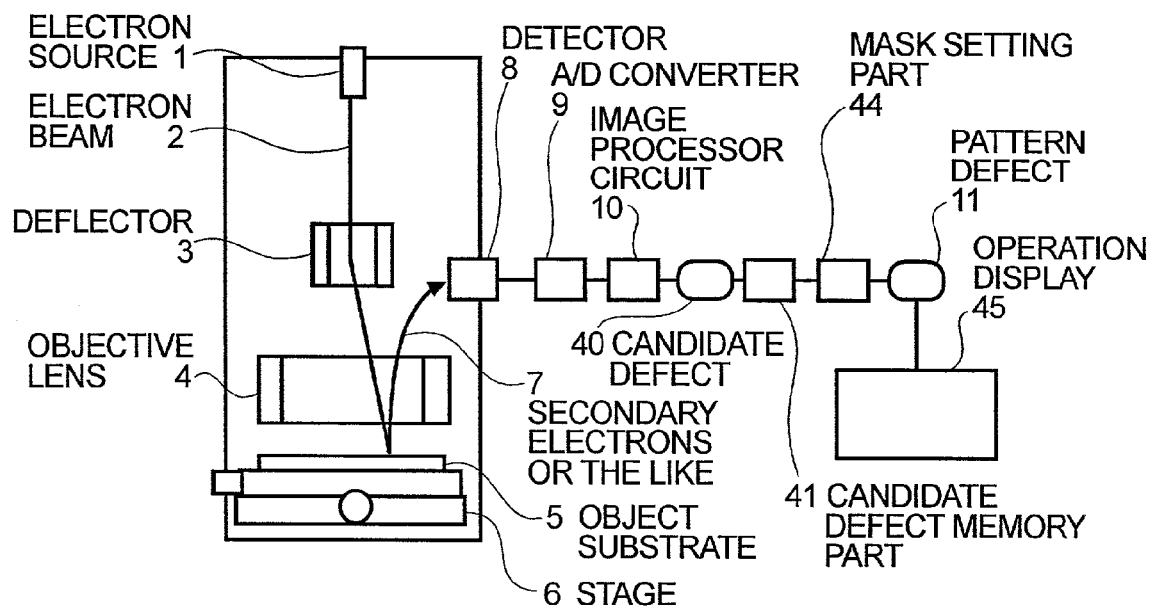
FIG. 4 is a schematic diagram of an electron-beam pattern inspection apparatus, showing an arrangement of first problem-solving means according to the present invention.
Figure 12:
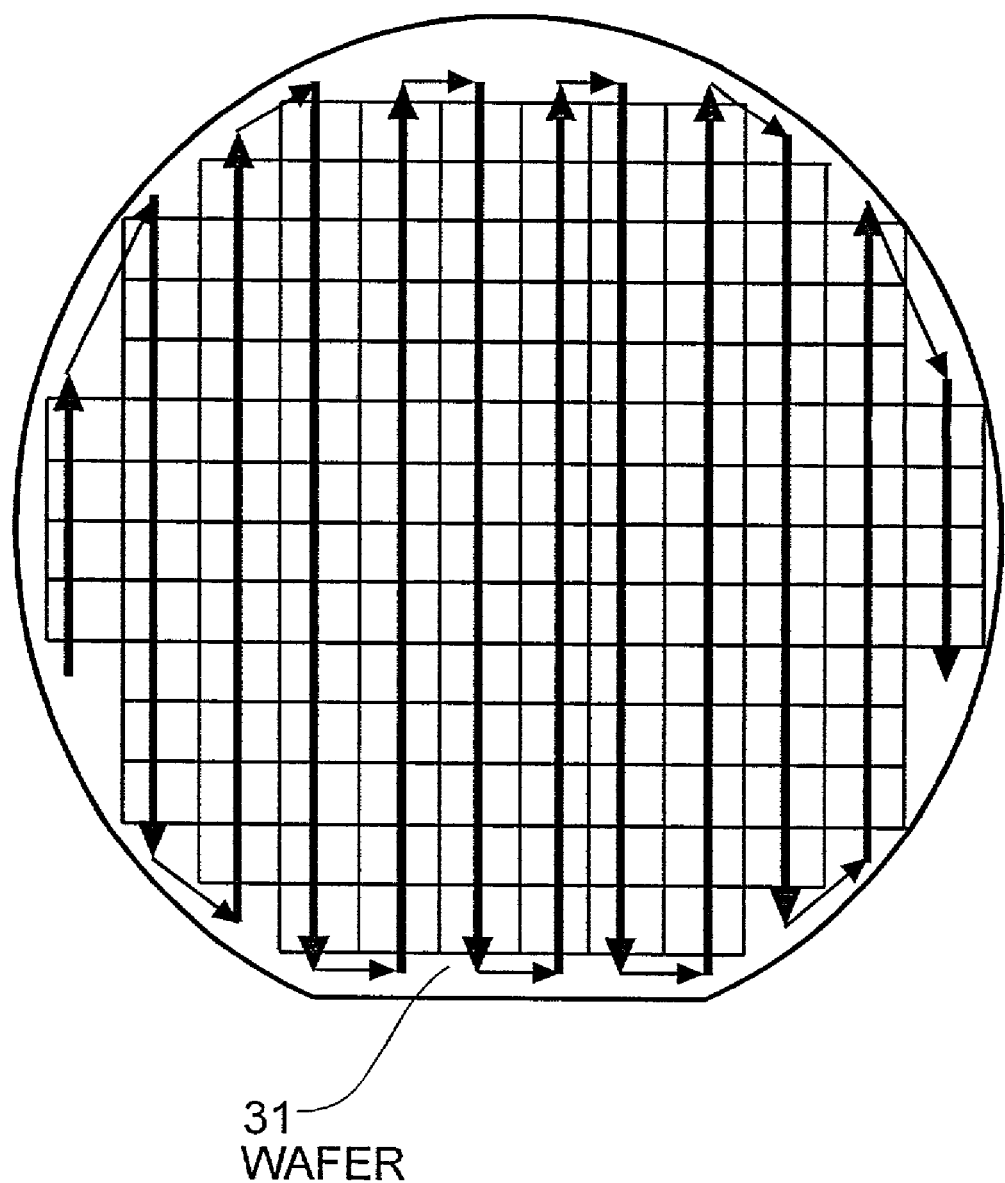
FIG. 12 is a plan view of a wafer, showing a scanning sequence in the first preferred embodiment of the present invention.

The trial inspection initial screen comprises a map display part 55, a recipe creation end button 133, a recipe save button 134, a recipe creation item selection button 142, an inspection start button 143, and an inspection end bit ton 144. The user sets the mouse operation command button 140 to a selection mode. Then, by clicking a die on the map display part 55, the user can select/deselect the die for trial inspection. Each die can thus be selected for trial inspection. After selecting any die for trial inspection, the user presses the inspection start button 143 to start trial inspection. When trial inspection is started, the stage 6 is driven for movement to a scanning start position of the region to be inspected on the wafer 31 mounted thereon. A pre-measured offset value inherent in the wafer 31 is added to the offset 112, and the Z sensor 113 is made effective. Then, along the scanning line 33 shown in FIG. 3, the stage 6 is scanned in the Y direction. In synchronization with this stage scanning, the deflector 105 is scanned in the X direction. During a period of effective scanning, a voltage to the blanking plate 63 is turned off to let the electron beam 2 fall on the wafer 31 for scanning the surface thereof. Backscattered electrons or secondary electrons produced from the wafer 31 are detected by the detector 8, and through the A/D converter 9, a digital image of the stripe region 34 is attained. The digital image thus attained is stored into the memory 109. After completion of the scanning operation of the stage 6, the Z sensor 113 is made ineffective. The entire region of interest can be inspected by repeating stage scanning. In cases were the entire surface of the wafer 31 is inspected, the scanning sequence shown in FIG. 12 is adopted.

When the detection position A 35 is selected in the image processor circuit 10, an image attained at the detection position A 35 is compared with an image attained at the detection position B 36, which has been stored in the memory 109. If any difference is found in the comparison, the difference is extracted as a candidate defect 40 to prepare a list of pattern defects 11. The list of pattern defects 11 thus prepared is sent to the general control part 110. In the general control part 110, feature quantity data of each pattern defect 11 is taken out of the candidate defect memory part 41. A pattern defect 11 located in the mask region 42, which has been registered in a recipe, is flagged as a masked defect 43 (feature quantity data thereof is flagged). After completion of inspection of the entire region of interest, the user opens a trial inspection defect check screen shown in FIG. 13.

Figure 14:
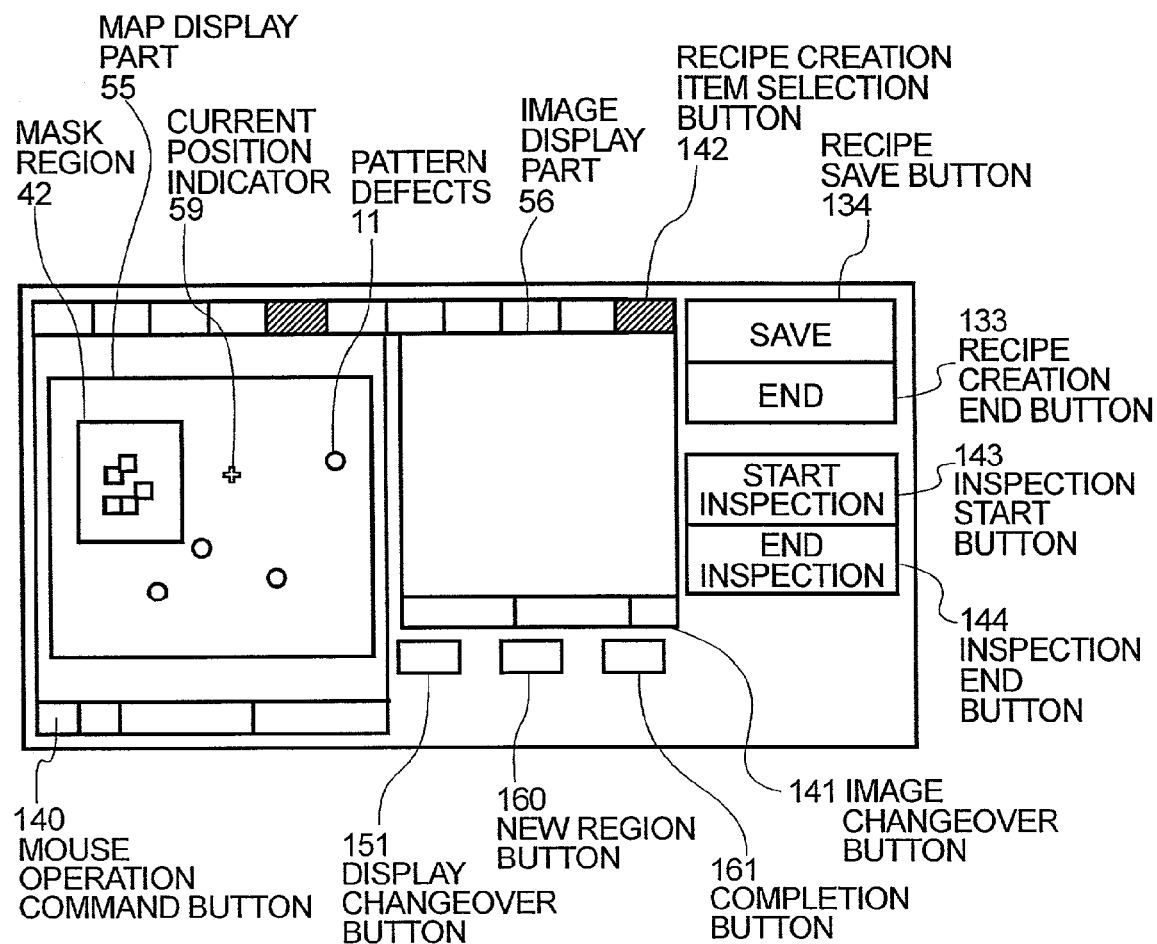
FIG. 14 is a diagram showing a mask region setting screen for recipe creation in the first preferred embodiment of the present invention.

The trial inspection defect check screen comprises a defect display editing part 150 for displaying feature quantity data of defects and editing classification thereof, a map display part 55 in which a current position indicator 59 indicating the current position and class code symbols of pattern defects 11 are displayed on a layout of the wafer 31, an image display part 56 in which an image taken at the current position is displayed, a display changeover button 151 for turning on/off masked defects 43, and other buttons which have already been described. The user sets the mouse operation command button 140 to the selection mode, and then clicks any pattern defect 11 indicated on the nap display part 55. Thus, an image of the pattern defect 11 is presented on the image display part 56, and feature quantity data thereof is presented on the defect display editing part 150. On the defect display editing part 150, the pattern defect 11 is subjected to classification according to the image and feature quantity data thereof, i.e., a class code is assigned to the feature quantity data of the pattern defect 11. At this step, if it is desired to treat the pattern defect 11 as a masked defect, a particular class code is assigned thereto. Thus, it can be identified as a masked defect on the map display part 55. After completion of the defect classification, the user makes a transition to a mask region setting screen, as shown in FIG. 14, by using the recipe creation item selection button, or the user returns to the trial inspection initial screen by pressing the inspection end button.

The mask region setting screen comprises a map display part 55 in which a current position indicator 59 indicating the current position, class code symbols of pattern, defects 11 and a mask region 42 are displayed on a layout of the wafer 31; an image display part 56 in which an image taken at the current position is displayed; a display changeover button 151 for turning on/off masked defects 43, a new region button 160 for creating a new mask region; a completion button 161 for indicating the end of creation of a new mask region; and other buttons which have already described. Note that the map display part 55 presents the entire die region. The current position indicator 59 and pattern defects 11 in the entire die region are indicated in representation of on-die coordinates.

The user sets the mouse operation command button 140 to the movement mode, and then clicks in the vicinity of a class code of any defect to be masked for making movement thereto. Thus, an image of the defect to be masked is presented on the image display part 56. If the user judges that a mask region should be formed, the user presses the new creation button 160 to select a region creation mode. In this mode, the user defines a mask region by clicking at the upper left corner and the lower right corner thereof on the image display part. The mask region thus defined (mask region 42) is indicated on the map display part 55. After creating the mask region, as mentioned above, the user can turn on/off masked defects 43 by pressing the display changeover button 151 to confirm the location of the defect to be masked. When the mask region 42 is set tp as required, the user presses the recipe save button 134 for saving data of the mask region 42 in a recipe.

After saving the data of the mask region 42, the user presses the completion button 161 to return to the trial inspection defect check screen. Further, on the trial inspection defect check screen, the user presses the inspection end button 144 to return to the trial inspection initial screen. Then, it is also possible for the user to select another die for trial inspection. For confirming and terminating the above-mentioned recipe creation session, the user presses the recipe creation end button 133. Upon completion of the recipe creation, the wafer 31 is unloaded back to the cassette 114.

The following description is directed to the inspection operation in which any candidate defect detected in other than the mask region is examined as a pattern defect. In the inspection operation, the user opens the startup screen shown in FIG. 9 on the operation display 45. On the slot selection part 130 of the start tp screen, the user selects a code number of a slot were the wafer 31 to be inspected is contained. Then, on the recipe selection part 131, the user specifies a product type of the wafer 31 and a process step thereof, and the user presses the inspection start button 330 for starting the inspection operation. After wafer loading, alignment and calibration are performed, inspection processing is carried out. Then, defect check and defect data output are performed, and wafer unloading is carried out at the end of inspection. The inspection processing and defect check, which form essential parts of the present invention, will now be described.

When the user presses the inspection start button 330 to indicate the start of inspection, the stage 6 is driven for movement to a scanning start position of the region to be inspected on the wafer 31 mounted thereon. A pre-measured offset value inherent in the wafer 31 is added to the offset 112, and the Z sensor 113 is made effective. Then, along the scanning line 33 shown in FIG. 3, the stage 6 is scanned in the Y direction. In synchronization with this stage scanning, the deflector 105 is scanned in the X direction. During a period of effective scanning, a voltage to the blanking plate 63 is turned off to let the electron beam 2 fall on the wafer 31 for scanning the surface thereof. Backscattered electrons or secondary electrons produced from the wafer 31 are detected by the detector 8, and through the A/D converter 9, a digital image of the stripe region 34 is attained. The digital image thus attained is stored into the memory 109. After completion of the scanning operation of the stage 6, the Z sensor 113 is made ineffective. The entire region of interest can be inspected by repeating stage scanning. In cases where the entire surface of the wafer 31 is inspected, the scanning sequence shown in FIG. 12 is adopted.

Figure 15:
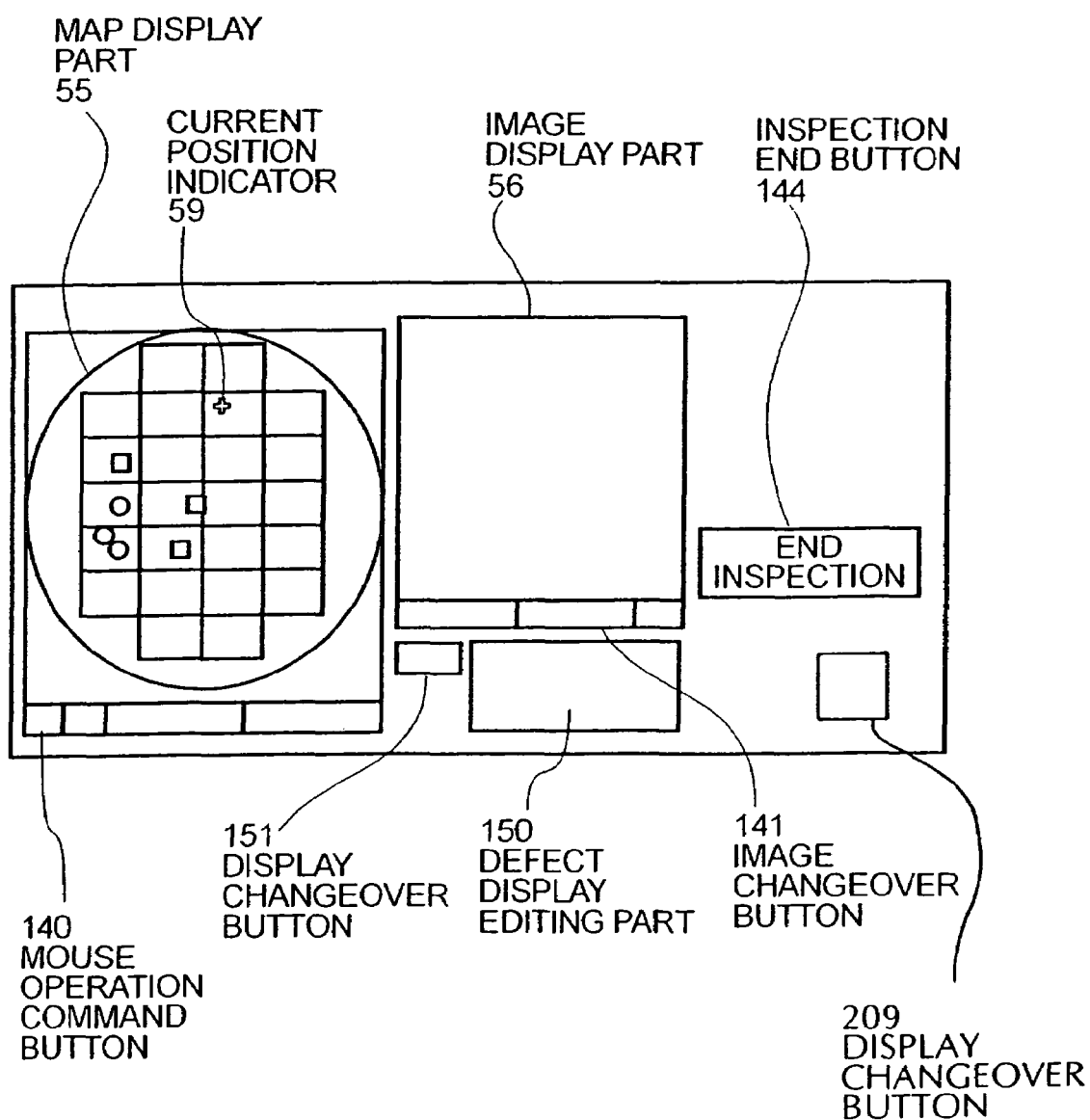
FIG. 15 is a diagram showing an inspection defect check screen in the first preferred embodiment of the present invention.

When the detection position A 35 is selected in the image processor circuit 10, an image attained at the detection position A 35 is compared with an image attained at the detection position B 36, which has been stored in the memory 109. If any difference is formed in comparison, the difference is extracted as a candidate defect 40 to prepare a list of pattern defects 11. The list of pattern defects 11 thus prepared is sent to the general control part 110. In the general control part 110, feature quantity data of each pattern defect 11 is taken out of the candidate defect memory part 41. A pattern defect 11 located in the mask region 42, which has been registered in a recipe, is flagged as a masked defect 43 (feature quantity data thereof is flagged). After completion of inspection of the entire region of interest, the inspection defect check screen shown in FIG. 15 is opened.

The inspection defect check screen comprises a defect display editing part 150 for displaying feature quantity data of defects and editing classification thereof, a map display part 55 in which a current position indicator 59 indicating the current position and class code symbols of pattern defects 11 are displayed on a layout of the wafer 31, an image display part 56 in which an image taken at the current position is displayed, a display changeover button 151 for turning on/off masked defects 43, and an inspection end button 144 for indicating the end of inspection.

The user sets the mouse operation command button 140 to the selection mode, and then clicks any pattern defect 11 indicated on the map display part 55. Thus, an image of the pattern defect 11 is presented on the image display part 56, and feature quantity data thereof is presented on the defect display editing part 150. On the defect display editing part 150, the pattern defect 11 is subjected to classification according to the image and feature quantity data thereof, i.e., a class code is assigned to the feature quantity data of the pattern defect 11. Using the display changeover button 151, the user can turn on/off masked defects 43 to check for any pattern defect in the mask region 41. To terminate the inspection defect check session mentioned above, the user presses the inspection end button 144. Each classified pattern defect 11 and feature quantity data thereof are stored into memory means (not shown) in the general control part 110, and also delivered to external memory means (not shown) through a communication line (not shown) or to other inspection/observation means (not shown). Then, control is returned to the initial screen.

According to one aspect of the first preferred embodiment, the entire surface of each wafer can be inspected using a SEM image thereof without regard to pattern defects in the mask region 42, i.e., true pattern defects 57 alone can be indicated to the user for easy identification thereof.

Further, according to another aspect of the first preferred embodiment, it is also possible to display masked defects in the mask region 42. Therefore, in cases where rough patterning is used to form a redundant power wiring layer, the degree of roughness in patterning can be examined by turning on/off the masked defects.

Still further, according to another aspect of the first preferred embodiment, the mask region 42 can be set so as to mask false defects which have been identified under actual inspection conditions. It is therefore possible for the user to define proper masking.

Furthermore, according to another aspect of the first preferred embodiment, a different mask region 42 can be created additionally. Therefore, in cases where masking has been defined using an object containing a small degree of random variation, the user can set up a new mask region additionally for providing proper masking as required.

In a first modified form of the first preferred embodiment, mask region management may be implemented in a part of image processing function hardware, instead of using the general control part that is a computer system. In this modified arrangement, essentially the same functionality is provided. Since the number of detectable defects is limited in terms of output capacity, this limitation can be removed by using image processing function hardware for mask region management.

In a second modified form of the first preferred embodiment, plural kinds of mask regions may be set up while only one kind of mask region has been treated in the forgoing description. In this modified arrangement, false defects due to plural kinds of causes can be classified for defect data management. By turning on/off indications of false defects according to each kind of cause, the user can check the conditions thereof. Thus, it is possible for the user to preclude only minimum false defects for carrying out proper inspection.

In a third modified form of the first preferred embodiment, a mask region on the mask region setting screen may be automatically defined as a rectangular region having a size approximately two times as large as the projection length of any false defect not to be detected. By merging neighboring mask regions, a mask region is determined using data of pattern defects classified without intervention of the user. In this modified arrangement, a flask region can be generated precisely through automatic operation. For example, masking at hundreds of points can be provided automatically so as to allow for easy identification. As a further modified form of this modification, there may be provided an arrangement in which an automatically determined mask region can be redefined or edited.

In a fourth modified form of the first preferred embodiment, a mask region may be determined using design data in inspection of rough patterning for power wiring, ion implantation, or the like. In this modified arrangement, the user can set up a mask region for each kind of false defect while saving the time of input.

In a fifth modified form of the first preferred embodiment, pattern defects are indicated on layout information at a networked CAD display terminal instead of being indicated on layout information stored in the inspection apparatus. In this modified arrangement, possible defects on each layer in rough patterning and fine patterning can be identified with ease.

Embodiment 2

Figure 16:
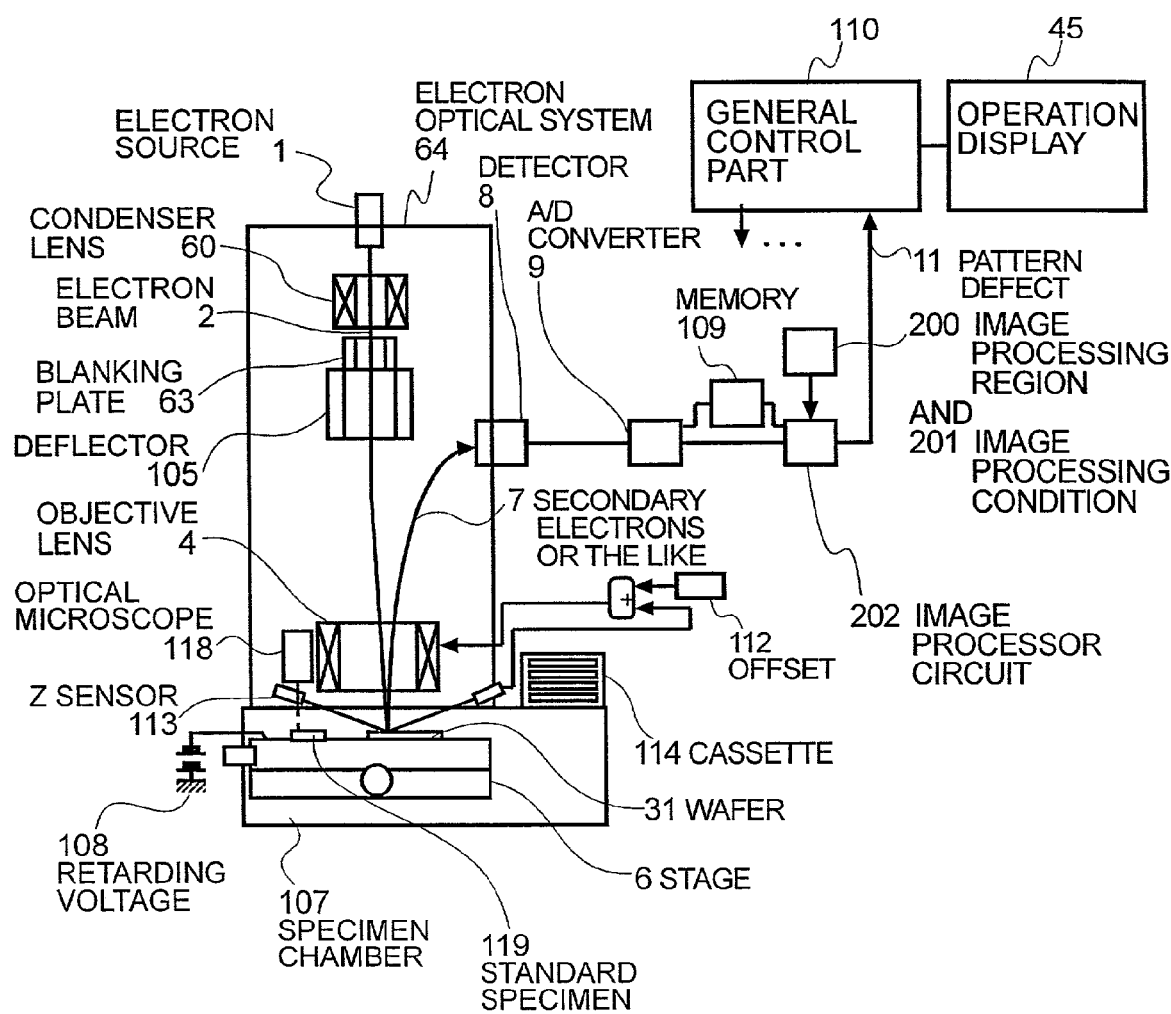
FIG. 16 is a schematic diagram showing the configuration of an electron-beam pattern inspection apparatus in a second preferred embodiment of the present invention.

A second preferred embodiment of the present invention will be described. FIG. 16 shows an example of the configuration of an electron-beam pattern inspection apparatus according to the second preferred embodiment of the present invention. The electron-beam pattern inspection apparatus comprises an electron optical system including: an electron source 1, for emitting an electron beam 2 from an electron gun in which the electron beam 2 from the electron source 1 is extracted and accelerated by an electrode to produce a virtual electron source at a predetermined point through an electrostatic or magnetic field superimposing lens; a condenser lens 60 for converging the electron beam 2 from the virtual electron source at a predetermined convergence point; a blanking plate 63 which is equipped in the vicinity of the convergence point of the electron beam 2 for turning on/off the electron beam 2; a deflector 105 for deflecting the electron beam 2 in the X and Y directions; and an objective lens 4 for converging the electron beam 2 onto an object substrate.

Further, the electron-beam pattern inspection apparatus comprises a specimen chamber 107 in which the object substrate (wafer 31) is held in a vacuum; a stage 6 where the wafer 31 is mounted and to which a retarding voltage 108 is applied for enabling detection of an image at an arbitrary position; and a detector 8 for detecting secondary electrons 7 or the like produced from the object substrate to output a detected analog signal. An A/D converter 9 is provided for converting the detected analog signal into a digital image, which is stored in a memory 109 for storing digital image data, and an image processor circuit 202 compares the converted digital image with a reference digital image stored in the memory 109 and identifies a difference, found in the comparison by changing an image processing condition 201 for each image processing region 200, as a pattern defect 11. A general control part 110 is provided, in which feature quantity data of each pattern defect 11, such as coordinate data, projection length data and shape data, is handled (control lines from the general control part 110 are not shown in FIG. 16); and an operation display 45 is provided on which data of pattern defects 11 is displayed, an image of a selected pattern defect 11 is displayed, and each image processing region 200 is displayed or edited.

Still further, the electron-beam pattern inspection apparatus comprises a keyboard, a mouse and a knob (not shown) for operation and control; a Z sensor 113 for measuring the height level of each wafer 31 to maintain a focal point of a detected digital image through control of a current applied to the objective lens by adding an offset 112; a loader (not shown) for loading the wafer 31 from its cassette 114 to the specimen chamber 107 and unloading the wafer 31 from the specimen chamber 107 to the cassette 114; an orientation flat detector (not shown) for positioning the wafer 31 according to the circumferential shape of the wafer 31; an optical microscope 118 for allowing observation of a pattern on the wafer 31; and a standard specimen 119 which is set on the stage 6.

Operations in the second preferred embodiment include a conditioning operation, in which an image processing region 200 and an image processing condition 201 thereof are set up, and an inspection operation, in which pattern defects 11 are detected.

In the conditioning operation, the user opens the startup screen shown in FIG. 9 on the operation display 45. On a slot selection part 130 of the startup screen, the user selects a code number of a slot where the wafer 31 to be inspected is contained. Then, on a recipe selection part 131, the user specifies a product type of the wafer 31 and a process step thereof, and the user presses a recipe creation start button 132 for starting the conditioning operation. The conditioning operation includes contrast setting for the electron optical system, pattern layout setting for the wafer 31, pattern positioning alignment for the wafer 31, calibration in which a signal level of the wafer 31 is checked at a position were the signal level is indicated accurately, inspection condition setting image processing region setting for specifying an image processing region 200 and an image processing condition 201 thereof, and setup condition check in trial inspection. The contrast setting, image processing region setting, and trial inspection, which form essential parts of the present invention, will now be described.

The general control part 110 provides operational instructions to each part in the following manner. First, the general control part 110 issues an operational instruction to the loader (not shown) so that the loader takes the wafer 31 out of the cassette 114. Then, through the use of the orientation flat detector (not shown), the circumferential shape of the wafer 31 is checked, and the wafer 31 is positioned according to the result of this check. The wafer 31 is then mounted on the stage 6, and the specimen chamber 107 is evacuated. Simultaneously, the electron optical system and the retarding voltage 108 are conditioned. A voltage is applied to the blanking plate 63 to turn off the electron beam 2. The stage 6 is moved so that the standard specimen 119 can be imaged, and an output of the Z sensor 113 is made effective. While a focal point of the electron beam 2 is maintained at a position corresponding to "a value detected by the Z sensor 113+an offset 112", raster scanning is performed by the deflector 105. In synchronization with this raster scanning, the voltage applied to the blanking plate 63 is turned off so that the wafer 31 is irradiated with the electron beam 2 as required. Backscattered, electrons or secondary electrons produced from the wafer 31 are detected by the detector 8, which then outputs a detected analog signal. Through the A/D converter 9, the detected analog signal is converted into a digital image. By changing the offset 112, a plurality of digital images are detected, and in the general control part 110, an optimum offset for maximizing the sum of image differential values is determined. The optimum offset 111 thus determined is set up as the current offset value.

After the optimum offset is established, the output of the Z sensor 113 is made ineffective and a screen transition is made to a contrast adjustment screen, such as shown in FIG. 10. The contrast adjustment screen comprises: a map display part 55 having a map display area, a button for controlling display of the entire wafer or die map, and a mouse operation command button 140 for controlling position movement or item selection by the use of the mouse 121 (not shown); an image display part 56 having an image display area and an image changeover button 141 for setting an image magnification, selecting an optical micrograph image attained through the optical microscope 118 or a SEM image attained through the electron optical system, and specifying a kind of image; a recipe creation item selection button 142; a recipe creation end button 133; and a recipe save button 134. On the contrast adjustment screen, the user sets the mouse operation command button 140 to a movement mode, and performs movement on the map by clicking the mouse to view an image at the current position on the image display part. Then, the user assigns an adjustment item of the electron optical system to the knob, and adjusts each part of the electron optical system to attain proper contrast.

The recipe creation end button 133 is used for terminating recipe creation; the recipe save button 134 is used for saving recipe condition data; and the recipe creation item selection button 142 is used for setting another condition and issuing an instruction for screen transition. These buttons are available on all the screens. To open a trial inspection initial screen, such as shown in FIG. 11, the user sets the recipe creation item selection button 142 to a trial inspection item.

The trial inspection initial screen comprises a map display part 55, a recipe creation end button 133, a recipe save button 134, a recipe creation item selection button 142, an inspection start button 143, and an inspection end button 144. The user sets the mouse operation command bitten 140 to a selection mode. Then, by clicking a die on the map display part 55, the user can select/deselect a die for trial inspection. Each die can thus be selected for trial inspection. After selecting any die for trail inspection, the user presses the inspection start button 143 to start trial inspection. When trial inspection is started, the stage 6 is driven for movement to a scanning start position of the region to be inspected on the wafer 31 mounted thereon.

A pre-measured offset value inherent in the wafer 31 is added to the offset 112, and the Z sensor 113 is made effective. Then, along the scanning line 33 shown in FIG. 3, the stage 6 is scanned in the Y direction. In synchronization with this stage scanning, the deflector 105 is scanned in the X direction. During a period of effective scanning, a voltage to the blanking plate 63 is turned off to let the electron beam 2 fall on the wafer 31, for scanning the surface thereof. Backscattered electrons or secondary electrons produced from the wafer 31 are detected by the detector 8, and through the A/D converter 9, a digital image of the stripe region 34 is attained. The digital image thus attained is stored into the memory 109. After completion of the scanning operation of the stage 6, the Z sensor 113 is made ineffective. The entire region of interest can be inspected by repeating stage scanning. In cases where the entire surface of the wafer 31 is inspected, the scanning sequence shown in FIG. 12 is adopted.

Figure 13:
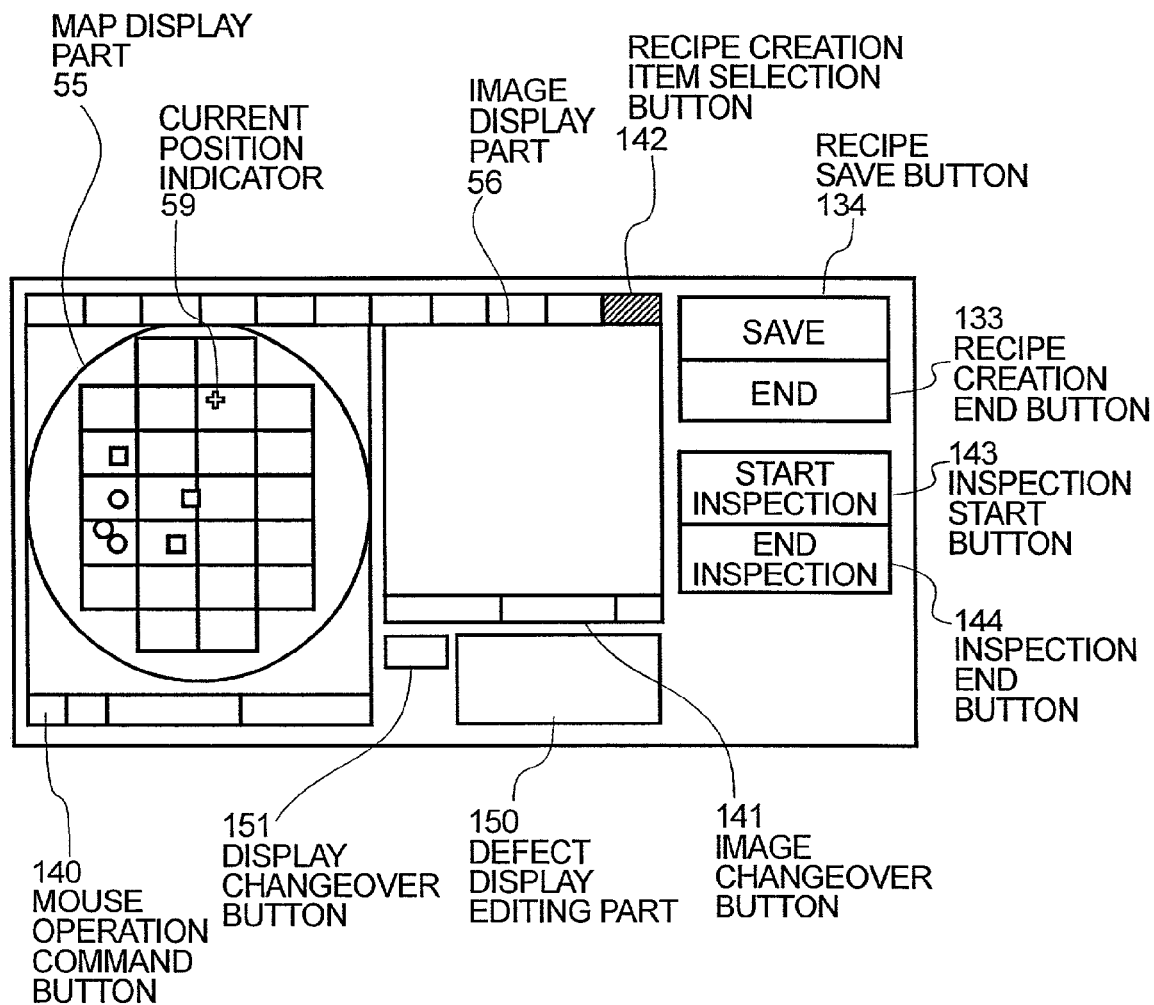
FIG. 13 is a diagram showing a trial inspection defect check screen for recipe creation in the first preferred embodiment of the present invention.

When the detection position A 35 is selected in the image processor circuit 202, an image attained at the detection position A 35 is compared with an image attained at the detection position B 36, which has been stored in the memory 109. If any difference is found in comparison, the difference is extracted as a pattern defect 11 to prepare a list of pattern defects 11. The list of pattern defects 11 thus prepared is sent to the general control part 110. After completion of inspection of the entire region of interest, the user opens a trial inspection defect check screen, such as shown in FIG. 13.

The trial inspection defect check screen comprises a defect display editing part 150 for displaying feature quantity data of defects and editing classification thereof, a map display part 55 in which a current position indicator 59 indicating the current position and class code symbols of pattern defects 11 are displayed on a layout of the wafer 31, an image display part 56 in which an image taken at the current position is displayed, a display changeover button 151 for turning on/off masked defects 43, and other buttons which have already been described.

Figure 17:
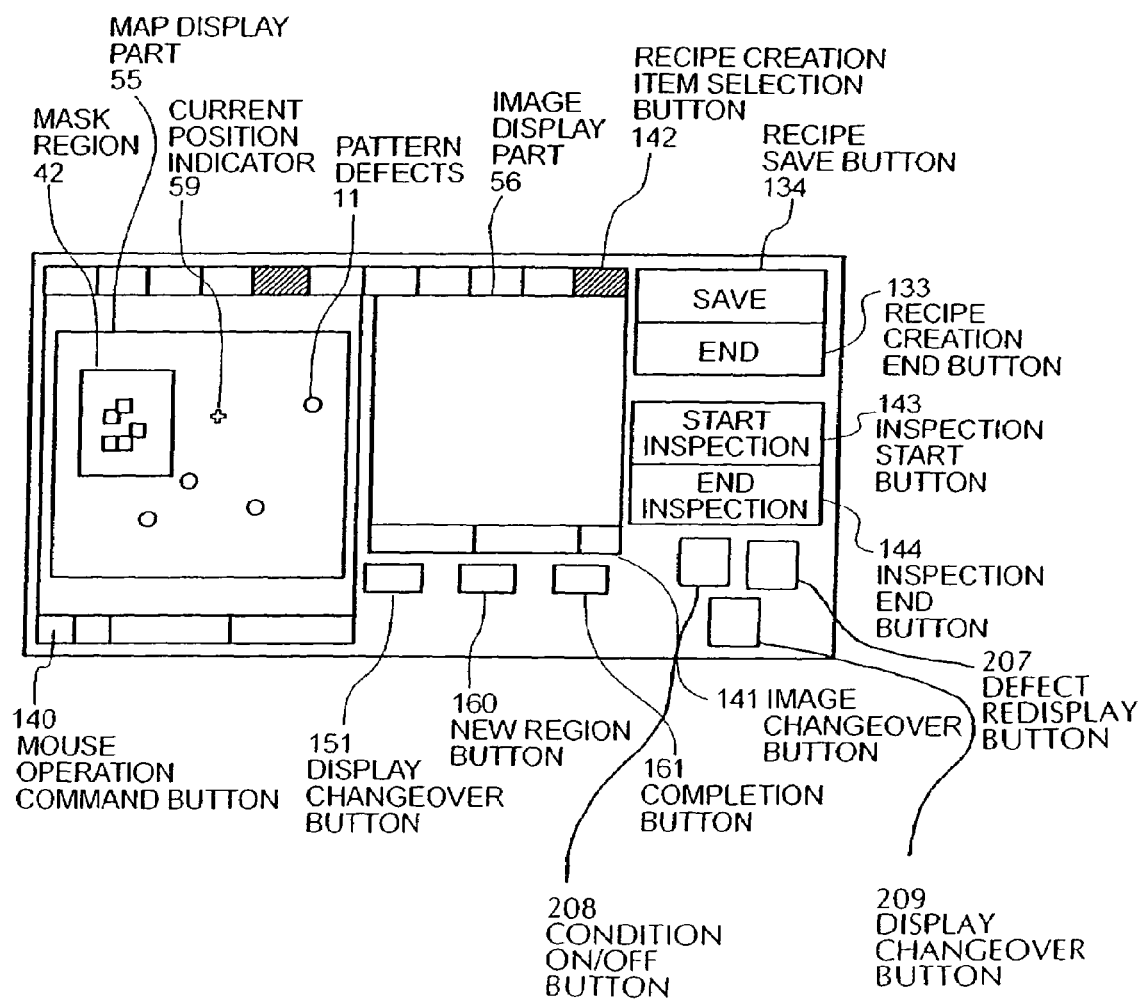
FIG. 17 is a diagram showing an image processing region setting screen for recipe creation in the second preferred embodiment of the present invention.

The user sets the mouse operation command button 140 to the selection mode, and then clicks any pattern defect 11 indicated on the map display part 55. Thus, an image of the pattern defect 11 is presented on the image display part 56, and feature quantity data thereof is presented on the defect display editing part 150. On the defect display editing part 150, the pattern defect 11 is subjected to classification according to the image and feature quantity data thereof, i.e., a class code is assigned to the feature quantity data of the pattern defect 11. At this step, if it is desired to treat the pattern defect 11 as a masked defect, a particular class code is assigned thereto. Thus, it can be identified as a masked defect on the map display part 55. After completion of the defect classification, the user makes a transition to an image processing region setting screen shown in FIG. 17 by using the recipe creation item selection button, or the user returns to the trial inspection initial screen by pressing the inspection end button.

The image processing region setting screen comprises a map display part 55 in which a current position indicator 59 indicating the current position, class code symbols of pattern defects 11, and an image processing region 200 are displayed on a layout of the wafer 31; an image display part 56 in which an image taken at the current position is displayed; a defect redisplay button 207 for defect indication based on feature quantity image data of each pattern defect 11; a new region button 160 for creating a new region; a completion button 161 for indicating the end of creation of a new region, and other buttons which have already described. Note that the map display part 55 presents the entire die region. The current position indicator 59 and pattern defects 11 in the entire die region are indicated in representation of on-die coordinates. The user sets the mouse operation command button 140 to the movement mode, and then clicks in the vicinity of a class code of any defect corresponding to the image processing condition 201 to be changed for making movement thereto. Thus, an image of the defect of interest is presented on the image display part 56.

If the user judges that the image processing condition 201 should be changed, the user presses the new creation button 160 to select a region creation mode. In this mode, the user defines a region by clicking at the upper left corner and the lower right corner thereof on the image display part, and the user provides a correspondence between an image processing condition number 206 of the region and a class code. Reference is made to the feature quantity image data 203 of a pattern defect 11 having the class code which corresponds to the image processing condition number, and the image processing condition 201 is set up for the image processing condition number so that all-defects detection will not be made by the image processor circuit or software in the general control part (computer). As required, the user adjusts the image processing condition 201 manually. Using a special condition on/off button 208, the user specifies whether or not the image processing condition 201 is to be applied at the time of inspection. On the map display part 55, the defined region is indicated as an image processing region 200 together with the image processing condition number. After creating the image processing region 200 as mentioned above, the user presses the defect redisplay button 207 to confirm that each pattern defect 11 belonging to the image processing region 200 is not indicated. When the image processing region 200 is set up as required, the user presses the recipe save bitten 134. Thus, data regarding the image processing region 200, the image processing condition number corresponding thereto, and the image processing condition 201 for each image processing number are saved in a recipe.

After saving the above data, the user presses the completion button 161 to return to the trial inspection defect check screen. Further, on the trial inspection defect check screen, the user presses the inspection end button 144 to return to the trial inspection initial screen. Then, it is possible for the user to select another die for trial inspection. For confirming and terminating the above-mentioned recipe creation session, the user presses the recipe creation end button 133. Upon completion of the recipe creation, the wafer 31 is unloaded back to the cassette 114.

The following describes the inspection operation. In the inspection operation, the user opens the startup screen shown in FIG. 9 on the operation display 45. On the slot selection part 130 of the startup screen, the user selects a code number of a slot where the wafer 31 to be inspected is contained. Then, on the recipe selection part 131, the user specifies a product type of the wafer 31 and a process step thereof, and the user presses an inspection start button 330 for starting the inspection operation. After wafer loading, alignment and calibration are performed, inspection processing is carried out. Then, defect check and defect data output are performed, and wafer unloading is carried out at the end of inspection. The inspection processing and defect check, which form essential parts of the present invention, will now be described.

When the user presses the inspection start button 330 to indicate the start of inspection, the stage 6 is driven for movement to a scanning start position of the region to be inspected on the wafer 31 mounted thereon. A pre-measured offset value inherent in the wafer 31 is added to the offset 112, and the Z sensor 113 is made effective. Then, along the scanning line 33 shown in FIG. 3, the stage 6 is scanned in the Y direction. In synchronization of this stage scanning, the deflector 105 is scanned in the X direction. During a period of effective scanning, a voltage to the blanking plate 63 is tuned off to let the electron beam 2 fall en the wafer 31 for scanning the surface thereof. Backscattered electrons or secondary electrons produced from the wafer 31 are detected by the detector 8, and through the A/D converter 9, a digital image of the stripe region 34 is attained. The digital image thus attained is stored into the memory 109. After completion of the scanning operation of the stage 6, the Z sensor 113 is made ineffective. The entire region of interest can be inspected by repeating stage scanning. In cases where the entire surface of the wafer 31 is to be inspected, the scanning sequence shown in FIG. 12 is adopted.

When the detection position A 35 is selected in the image processor circuit 202, an image attained at the detection position A 35 is compared with an image attained at the detection position B 36, which has been stored in the memory 109. If any difference is found in comparison, the difference is extracted as a pattern defect 11 to prepare a list of pattern defects 11. The list of pattern defects 11 thus prepared is sent to the general control part 110. After completion of inspection of the entire region of interest, an inspection defect check screen, such as shown in FIG. 15, is opened.

The inspection defect check screen comprises a defect display editing part 150 for displaying feature quantity data of defects and editing classification thereof, a map display part 55 in which a current position indicator 59 indicating the current position and class code symbols of pattern defects 11 are displayed on a layout of the wafer 31, an image display part 56 in which an image taken at the current position is displayed, a display changeover button 151 for turning on/off masked defects 43, and an inspection end button 144 for indicating the end of inspection. The user sets the mouse operation command button 140 to the selection mode, and then clicks any pattern defect 11 indicated on the map display part 55. Thus, an image of the pattern defect 11 is presented on the image display part 56, and feature quantity data thereof is presented on the defect display editing part 150. On the defect display editing part 150, the pattern defect 11 is subjected to classification according to the image and feature quantity data thereof, i.e., a class code is assigned to the feature quantity data of the pattern defect 11.

A display changeover button 209 is provided for turning on/off the display for the image processing condition 201 in the image processing region 200. With this button, the user can perform a display changeover according to whether or not the image processing condition 201 is applied to each pattern defect 11 in the image processing region 200. If, by using the special condition on/off button 208, the user has specified that the image processing condition 201 is to be applied at the time of inspection, a display changeover with the image display changeover button 209 is not available since the image processing condition 201 is already applied. To terminate the inspection defect check session mentioned above, the user presses the inspection end button 144. Each classified pattern defect 11 and feature quantity data thereof are stored into memory means (not shown) in the general control part 110, and they are also delivered to external memory means (not shown) through a communication line (not shown) or to other inspection/observation means (not shown). Then, control is returned to the initial screen.

According to one aspect of the second preferred embodiment, the entire surface of each wafer can be inspected using a SEM image thereof without regard to pattern defects in the image processing region 200, i.e., true pattern defects 57 only can be indicated to the user for easy identification thereof.

Further, according to another aspect of the second preferred embodiment, it is possible to display defects in the image processing region 200. Therefore, in cases where rough patterning is used to form a redundant power wiring layer, the degree of roughness in patterning can be examined by means of display changeover.

Still further, according to another aspect of the second preferred embodiment, an image processing condition can be set so that false defects identified under actual inspection conditions will not be detected. It is therefore possible for the user to specify a threshold properly just as required.

Furthermore, according to another aspect of the second preferred embodiment, a different image processing region 200 can be created additionally. Therefore, in cases where the image processing condition 201 has been defined using an object containing a small degree of random variation, the user can set up a new image processing region additionally to provide proper conditioning for image processing as required.

Moreover, according to another aspect of the second preferred embodiment, the image processing condition 201 is adjustable without completely deleting data of pattern defects 11 an the image processing region 200. Therefore, the user can adjust the image processing condition 201 so that false defect detection will be prevented as required while possible defects remain inspectable.

Still further, according to another aspect of the second preferred embodiment, in cases where, by using the special condition on/off button 208, the user has specified that the image processing condition 201 is not to be applied at the time of inspection, it is possible to alter the image processing region 200 and the image processing condition 201. Therefore, even if it becomes necessary to provide a different image processing condition due to variation in a fabrication process, the user has only to adjust the image processing condition 201. Thus, inspection can be carried out using feature quantity data acquired already.

Embodiment 3

A third preferred embodiment of the present invention will now be described.

Figure 18:
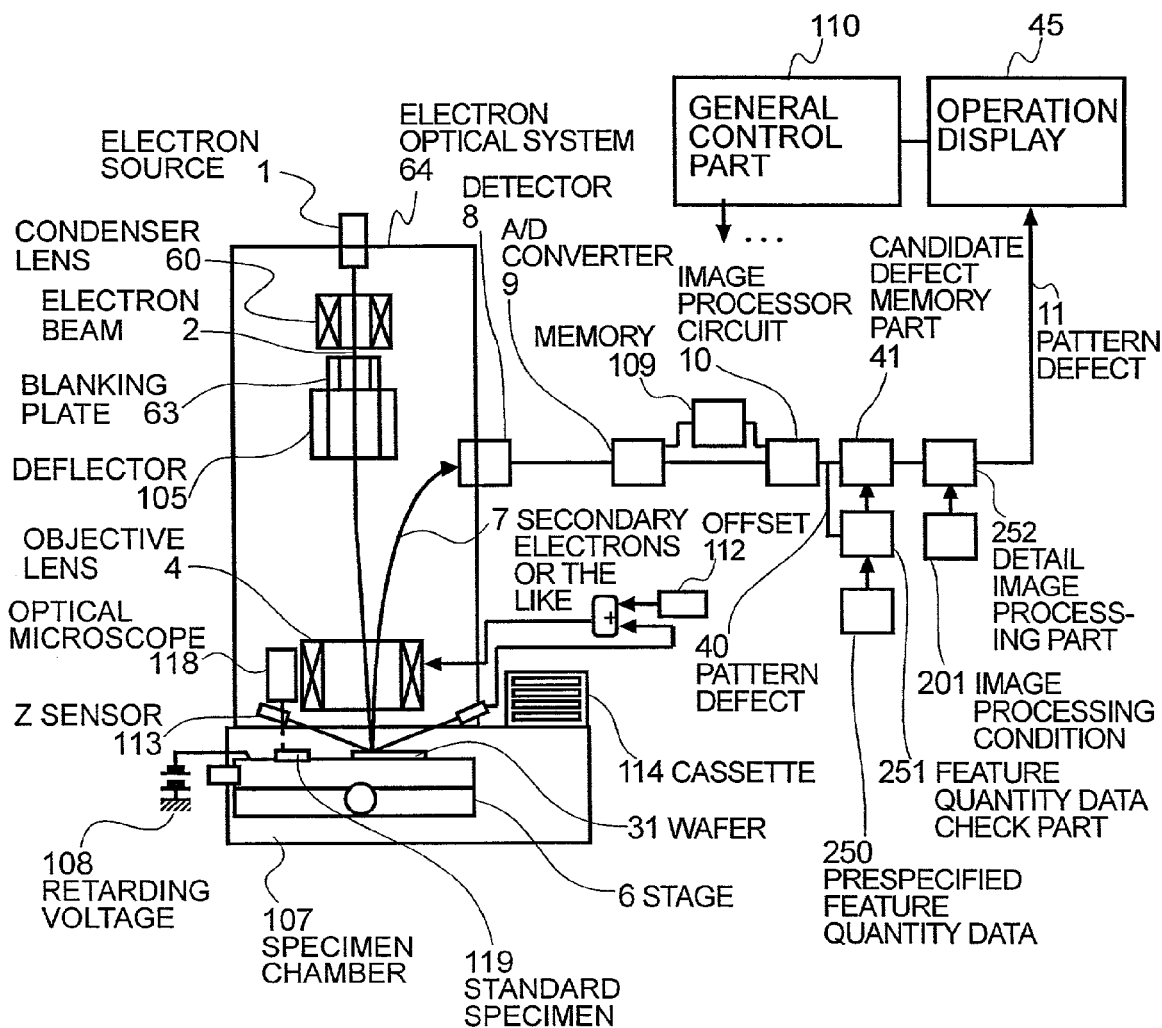
FIG. 18 is a schematic diagram showing the configuration of an electron-beam pattern inspection apparatus in a third preferred embodiment of the present invention.

FIG. 18 shows an example of the configuration of an electron-beam pattern inspection apparatus according to the third preferred embodiment of the present invention. The electron-beam pattern inspection apparatus comprises an electron optical system including: an electron source 1 for emitting an electron beam 2 in the form of an electron gun in which the electron beam 2 from the electron source 1 is extracted and accelerated by an electrode to produce a virtual electron source at a predetermined point through an electrostatic or magnetic field superimposing lens; a condenser lens 60 for converging the electron beam 2 from the virtual electron source at a predetermined convergence point; a blanking plate 63 which is equipped in the vicinity of the convergence point of the electron beam 2 for turning on/off the electron beam 2; a deflector 105 for deflecting the electron beam 2 in the X and Y directions; and an objective lens 4 for converging the electron beam 2 onto an object substrate 5.

Further, the electron-beam pattern inspection apparatus comprises: a specimen chamber 107 in which the object substrate (wafer 31) is held in a vacuum; a stage 6 where the wafer 31 is mounted and to which a retarding voltage 108 is applied for enabling detection of an image at an arbitrary position; and a detector 8 for detecting secondary electrons 7 or the like produced from the object substrate to output a detected analog signal. An A/D converter 9 is provided for converting the detected analog signal into a digital image, which is stored in a memory 109 for storing digital image data, and an image processor circuit 10 compares the converted digital image with a reference digital image stored in the memory 109 and identifies a difference found in the comparison as a candidate defect 40. A candidate defect memory part 41 is provided for storing feature quantity data 203 of each candidate defect 40, such as coordinate data, projection length data and shape data. A feature quantity check part 251 is provided in which feature quantity data 203 of each candidate defect 40 is received from the candidate defect memory part 41 and it is checked to see whether the candidate defect 40 meets prespecified feature quantity data 250. A detail image processing part 252 is provided in which, under an image processing condition 201 specified for each feature quantity data, a judgment for determining each pattern defect 11 is formed on the candidate defect 40 that has proved to meet the prespecified, feature quantity data 250 as determined by the feature quantity data check part 251, and a general control part 110 receives data of each pattern defect 11 from the detail image processing part 252 (control lines from the general control part 110 are not shown in FIG. 18). An operation display 45 is provided on which data of pattern defects 11 is displayed, an image of a selected pattern defect 11 is displayed, and the image processing region 200 is displayed or edited.

Still further, the electron-beam pattern inspection apparatus comprises a keyboard, a mouse and a knob (not shown)

for operation and control; a Z sensor 113 for measuring the height level of each wafer 31 to maintain a focal point of a detected digital image through control of a current applied to the objective lens by adding an offset 112; a loader (not shown) for loading the wafer 31 from its cassette 114 to the specimen chatter 107 and unloading the wafer 31 from the specimen chamber 107 to the cassette 114; an orientation flat detector (not shown) for positioning the wafer 31 according to the circumferential shape of the wafer 31; an optical microscope 118 for providing for observation of a pattern on the wafer 31; and a standard specimen 119 which is set en the stage 6.

Operations in the third preferred embodiment include a conditioning question, in which feature quantity data 250 and an image processing condition 201 thereof are set up, and an inspection operation, in which pattern defects 11 are detected.

In the conditioning operation, the user opens the startup seen shown in FIG. 9 on the operation display 45. On a slot selection part 130 of the startup screen, the user selects a code number of a slot where the wafer 31 to be inspected is contained. Then, on a recipe selection part 131, the user specifies a product type of the wafer 31 and a process step thereof, and the user presses a recipe creation start button 132 for starting the conditioning operation. Conditioning operation includes contrast setting for the electron optical system, pattern layout setting for the wafer 31, pattern positioning alignment for the wafer 31, calibration in which a signal level of the wafer 31 is checked at a position where the signal level is indicated accurately, inspection condition setting, image processing feature quantity data setting for specifying feature quantity data 250 and an image processing condition 201 thereof, and setup condition check in trial inspection. The contrast setting, image processing feature quantity data setting, and trial inspection, which form essential parts of the present invention, will now be described.

The general control part 110 provides operational instructions to each part in the following manner. First, the general control part 110 issues an operational instruction to the loader (not shown) so that the loader takes the wafer 31 out of the cassette 114. Then, through the use of the orientation flat detector (not shown), the circumferential shape of the wafer 31 is checked, and the wafer 31 is positioned according to the result of this check. The wafer 31 is then mounted on the stage 6, and the specimen chamber 107 is evacuated. Simultaneously, the electron optical system 106 and the retarding voltage 108 are conditioned. A voltage is applied to the blanking plate 63 to turn off the electron beam 2. The stage 6 is moved so that the standard specimen 119 can be imaged, and an output of the Z sensor 113 is made effective. While a focal point of the electron beam 2 is maintained at a position corresponding to "a value detected by the Z sensor 113+an offset 112", raster scanning is performed by the deflector 105. In synchronization with this raster scanning, the voltage applied to the blanking plate 63 is turned off so that the wafer 31 is irradiated with the electron beam 2 as required.

Backscattered electrons or secondary electrons produced from the wafer 31 are detected by the detector 8, which then outputs a detected analog signal. Through the A/D converter 9, the detected analog signal is converted into a digital image. By changing the offset 112, a plurality of digital images are detected, and in the general control part 110, an optimum offset for maximizing the sun of image differential values is determined. The optimum offset thus determined is set up as the current offset value. After the optimum offset is established, the output of the Z sensor 113 is made ineffective, and a screen transition is made to a contrast adjustment screen, such as shown in FIG. 10.

The contrast adjustment screen comprises: a map display part 55 having a map display area, a button for controlling display of the entire wafer or die, map, and a mouse operation command button 140 for controlling position movement or item selection by the use of the mouse (not shown); an image display part 56 having an image display area and an image changeover button 141 for setting an image magnification, selecting an optical micrograph image obtained through the optical microscope 118 or a SEM image obtained through the electron optical system, and specifying a kind of image; a recipe creation item selection button 142; a recipe creation end button 133; and a recipe save button 134.

On the contrast adjustment screen, the user sets the mouse operation command button 140 to a movement mode, and performs movement on the map by clicking the mouse to view an image at the current position on the image display part. Then, the user assigns an adjustment item of the electron optical system, to the knob, and adjusts each part of the electron optical system to attain proper contrast. The recipe creation end button 133 is used for terminating recipe creation; the recipe save button 134 is used for saving recipe condition data; and the recipe creation item selection button 142 is used for setting another condition and issuing an instruction for screen transition. These buttons are available on all the screens. To open a trial inspection initial screen, such as shown in FIG. 11, the user sets the recipe creation item selection button 142 to a trial inspection item.

The trial inspection initial screen comprises a map display part 55, a recipe creation end button 133, a recipe save button 134, a recipe creation item selection button 142, an inspection start button 143, and an inspection end bit ton 144. The user sets the mouse operation command button 140 to a selection mode. Then, by clicking a die on the map display part 55, the user can select/deselect the die for trial inspection. Each die can thus be selected for trial inspection. After selecting any die for trial inspection, the user presses the inspection start button 143 to start trial inspection. When trial inspection is started, the stage 6 is driven for movement to a scanning start position of the region to be inspected on the wafer 31 mounted thereon. A pre-measured offset value inherent in the wafer 31 is abed to the offset 112, and the Z sensor 113 is made effective. Then, along the scanning line 33 shown in FIG. 3, the stage 6 is scanned in the Y direction. In synchronization with this stage scanning, the deflector 105 is scanned in the X direction. During a period of effective scanning, a voltage to the blanking plate 63 is turned off to let the electron beam 2 fail on the wafer 31 for scanning the surface thereof.

Backscattered electrons or secondary electrons produced from the wafer 31 are detected by the detector 8, and through the A/D converter 9, a digital image of the stripe region 34 is obtained. The digital image thus obtained is stored into the memory 109. After completion of the scanning operation of the stage 6, the Z sensor 113 is made ineffective. The entire region of interest can be inspected by repeating stage scanning. In cases where the entire surface, of the wafer 31 is inspected, a scanning sequence shown in FIG. 12 is carried out.

Figure 19:
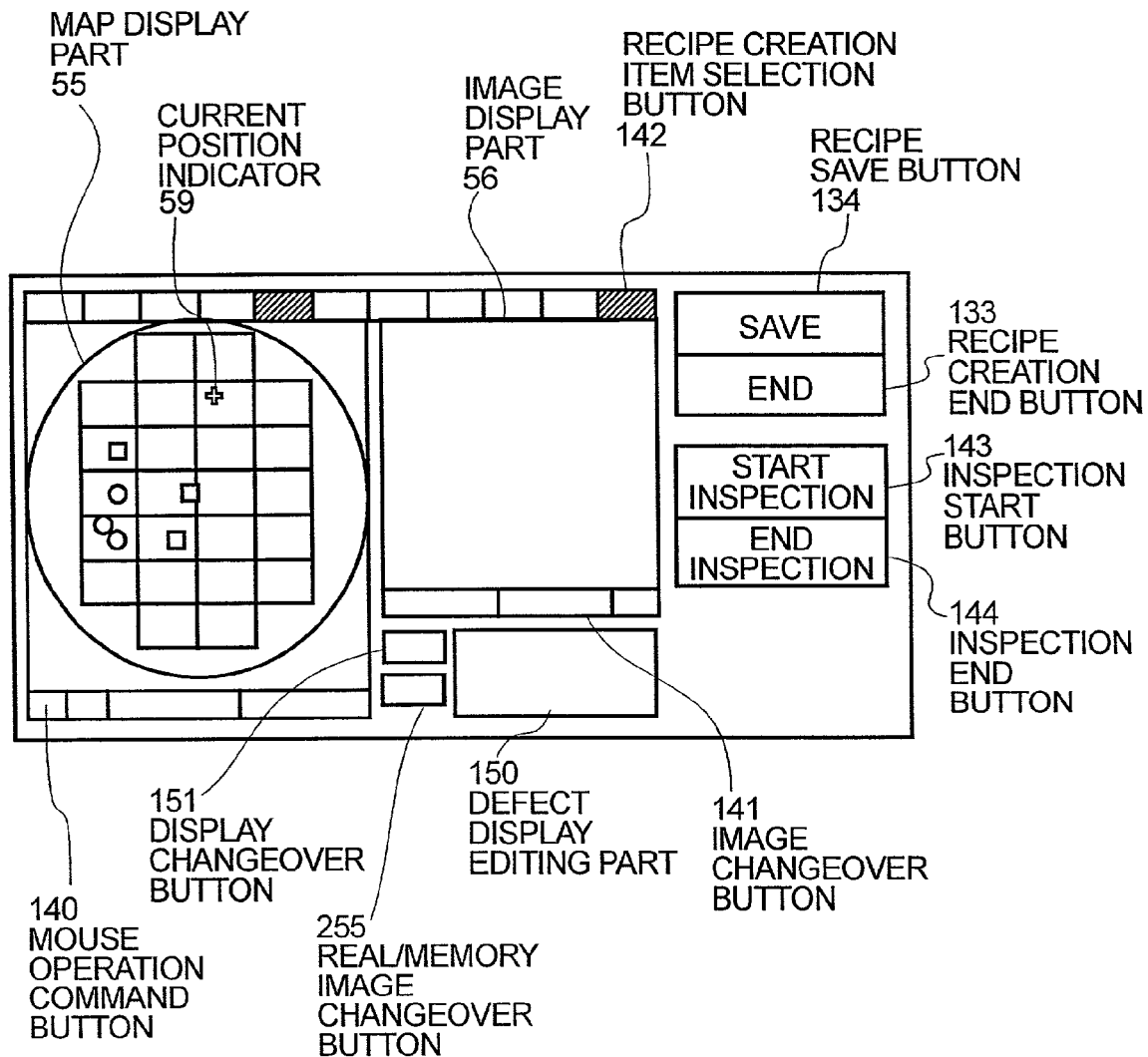
FIG. 19 is a diagram showing a defect check screen for recipe creation in the third preferred embodiment of the present invention.

When the detection position A 35 is selected in the image processor circuit 10, an image obtained at the detection position A 35 is compared with an image obtained at the detection position B 36, which has been stored in the memory 109. If any difference is found in comparison, the difference is extracted as a candidate defect 40 and feature quantity data of the candidate defect 40 is stored into the candidate defect memory part 41. Simultaneously at the feature quantity data check part 251, it is checked to see whether the candidate defect 40 meets prespecified feature quantity data 250 or not. If the candidate defect 40 meets the prespecified feature quantity data 250, data of the candidate defect 40 is sent to the detail image processing part 252. Then, in the detail image processing part 252, image processing is carried out under an image processing condition 201 determined for each prespecified feature quantity data to check whether the candidate defect 40 is a pattern defect 11 or not. If the candidate defect 40 is recognized as a pattern defect 11, an identification, code thereof stored in the candidate defect memory part 41 is sent to the general control part 110. After completion of inspection of the entire region of interest, a defect check screen, such as shown in FIG. 19, is opened.

Figure 20:
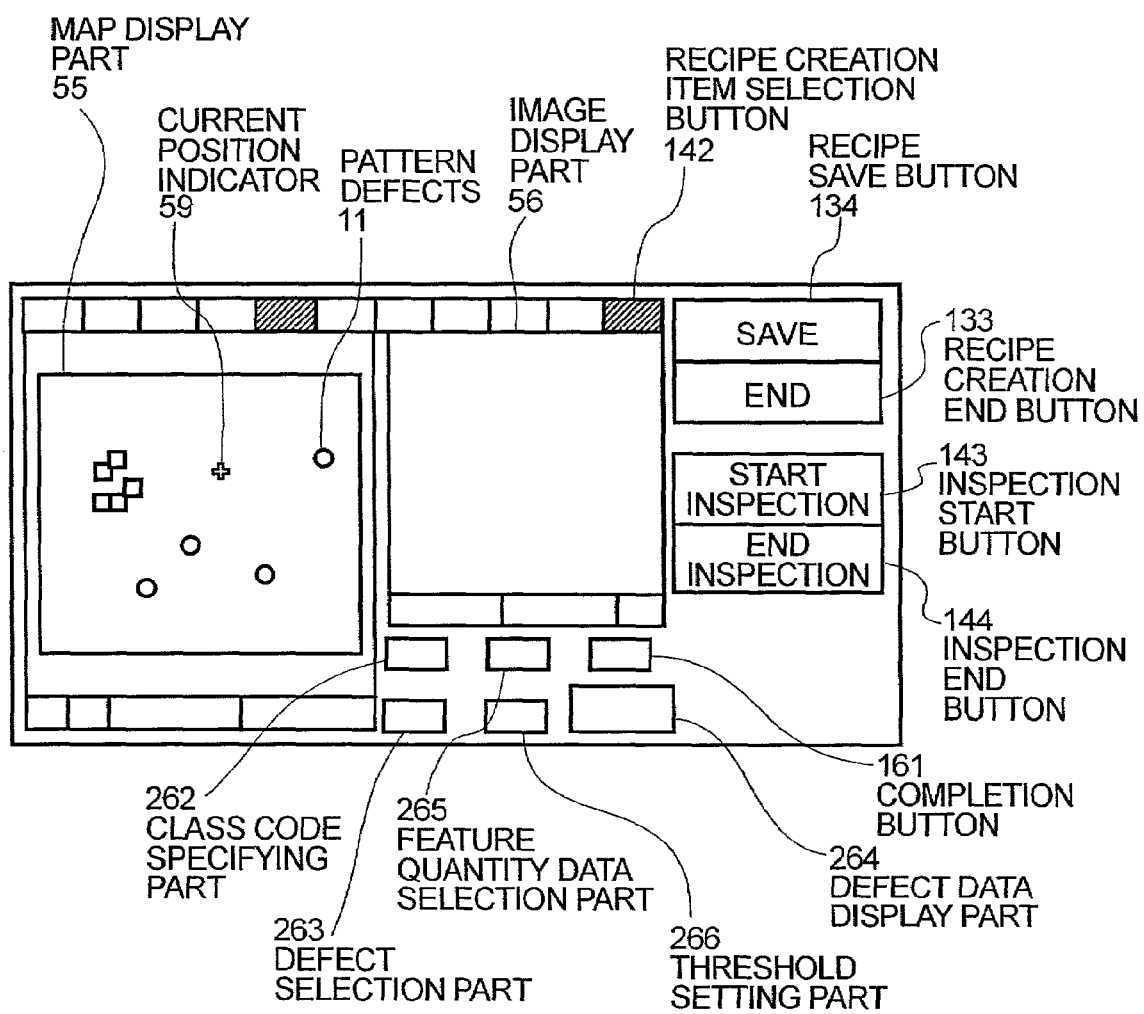
FIG. 20 is a diagram showing an image processing feature quantity data setup screen for recipe creation in the third preferred embodiment of the present invention.

The defect check screen comprises a defect display editing part 150 for displaying feature quantity data of defects and editing classification thereof; a map display part 55, in which a current position indicator 59 indicating the current position and class code symbols of pattern defects 11 are displayed on a layout of the wafer 31; an image display part 56, in which an image taken at the current position is displayed; a real/memory image display changeover button 255 for effecting a changeover between a real, image display and a memory image display, and other buttons which have already been described. The user sets the mouse operation command button 140 to the selection mode, and then clicks any pattern defect 11 indicated on the map display part 55. Then, if a real image selection has been made with the real/memory image changeover button 255, a coordinate location of the pattern defect 11 is taken for image acquisition. If a memory image selection has been made with the real/memory image changeover button 255, an image of the pattern defect 11 is presented on the image display part 56, and feature quantity data thereof is presented on the defect display editing part 150. On the defect display editing part 150, the pattern defect 11 is subjected to classification according to the image and feature quantity data thereof, i.e., a class code is assigned to the feature quantity data of the pattern defect 11. At this step, if it is desired to treat the pattern defect 11 as a defect not to be detected 58, a particular class code is assigned thereto. Thus, it can be identified as a defect not to be detected on the map display part 55. After completion of the defect classification, the user makes a transition to an image processing feature quantity data setting screen, as shown in FIG. 20, using the recipe creation item selection button, or the user returns to the trial inspection initial screen by pressing the inspection end button.

The image processing feature quantity data setting screen comprises a class code specifying part 262 for specifying a class code of interest 261; a defect selection part 263 for selecting defects having the class code of interest in succession; a feature quantity data specifying part 264 for specifying feature quantity data of each selected defect and feature quantity data 250 used as a selection criterion; a map display part 55; an image display part 56, in which an image of each defect 11 is displayed; an image processing condition setting part 265 for setting up an image processing condition number corresponding to an image processing condition 201 to be applied to an image selected by the feature quantity data specifying part 264; a defect redisplay button 207 for indicating on the map display part 55 the result of judgment attained after an evaluation image processing part 252 checks to see whether or not an image in the candidate defect memory part 41 is a pattern defect 11; a new feature quantity data creation button 266 for creating a new image processing condition number corresponding to prespecified feature quantity data 250; a completion button 161 for indicating the end of creation of new feature quantity data; and other buttons which have already described. The recipe save button 134 is provided for saving data in a recipe.

After saving the data, the user presses the completion button 161 to return to the trial inspection defect check screen. Further, en the trial inspection defect check screen, the user presses the inspection end button 144 to return to the trial inspection initial screen. Then, it is possible for the user to select another die for trial inspection. For confirming and terminating the above-mentioned session, the user presses the recipe creation end button 133. Upon completion of the recipe creation, the wafer 31 is unloaded back to the cassette 114.

The inspection operation will now be described. In the inspection operation, the user opens the startup screen shown in FIG. 9 on the operation display 45. On the slot selection part 130 of the startup screen, the user selects a code number of a slot where the wafer 31 to be inspected is contained. Then, on the recipe selection part 131, the user specifies a product type of the wafer 31 and a process step thereof, and the user presses an inspection start button 330 for starting the inspection operation. After wafer loading, alignment and calibration are performed, inspection processing is carried out. Then, defect check and defect data output are performed, and wafer unloading is carried out at the end of inspection. The inspection processing and defect check, which form essential parts of the present invention, will now be described.

When the user presses the inspection start button 330 to indicate the start of inspection, the stage 6 is driven for movement to a scanning start position of the region to be inspected on the wafer 31 mounted thereon. A pre-measured offset value inherent in the wafer 31 is added to the offset 112, and the Z sensor 113 is made effective. Then, along the scanning line 33 shown in FIG. 3, the stage 6 is scanned in the Y direction. In synchronization of this stage scanning, the deflector 105 is scanned in the X direction. During, a period of effective scanning, a voltage to the blanking plate 63 is turned off to let the electron beam 2 fall on the wafer 31 for scanning the surface thereof. Backscattered electrons or secondary electrons produced from the wafer 31 are detected by the detector 8, and through the A/D converter 9, a digital image of the stripe region 34 is obtained. The digital image thus attained is stored into the memory 109. After completion of the scanning operation of the stage 6, the Z sensor 113 is made ineffective. The entire region of interest can be inspected by repeating stage scanning. In cases where the entire surface of the wafer 31 is inspected, the scanning sequence shown in FIG. 12 is employed.

When the detection position A 35 is selected in the image processor circuit 202, an image obtained at the detection position A 35 is compared with an image obtained at the detection position B 36, which has been stored in the memory 109. If any difference is found in comparison, the difference is extracted as a candidate defect 40 and stored in the candidate defect memory part 41. Further, the feature quantity data check part 251 selects a candidate defect meeting the prespecified feature quantity data, and using an image processing condition 201 determined by an image processing condition number corresponding to the prespecified feature quantity data, the detail image processing part 252 formed a judgment on whether or not the candidate defect 40 is a pattern defect 11 so as to prepare a list of pattern defects 11. The list of pattern defects 11 thus prepared is sent to the general control part 110. After completion of inspection of the entire region of interest, a defect check screen such as shown in FIG. 15 is opened.

The defect check screen comprises a defect display editing part 150 for displaying feature quantity, data of defects and editing classification thereof; a map display part 55, in which a current position indicator 59 indicating the current position and class code symbols of pattern defects 11 are displayed on a layout of the wafer 31; an image display part 56 in which an image taken at the current position is displayed; a display changeover button 151 for turning on/off candidate defects 41 with pattern defects 11 indicated; and an inspection end bit ten 144 for indicating the end of inspection.

The user sets the mouse operation command button 140 to the selection mode, and then clicks any pattern defect 11 indicated on the map display part 55. Thus, an image of the pattern defect 11 is presented on the image display part 56, and feature quantity data thereof is presented on the defect display editing part 150. On the defect display editing part 150, the pattern defect 11 is subjected to classification according to the image and feature quantity data thereof, i.e., a class code is assigned to the feature quantity data of the pattern defect 11. A display changeover button 209 is provided for turning on/off the display for the image processing condition 201 in the image processing region 200. With this button, the user can perform a display changeover according to whether or not the image processing condition 201 is applied to each pattern defect 11 in the image processing region 200. If, by using the special condition on/off button 208, the user has specified that the image processing condition 201 is to be applied at the time of inspection, a display changeover with the image display changeover button 209, is not available, since the image processing condition 201 is already applied. To term mate the inspection defect check session mentioned above, the user presses the inspection end button 144. Each classified pattern defect 11 and feature quantity data thereof are stored into memory means (not shown) in the general control part 110, and they are also delivered to external memory means (not shown) through a communication line (not shown) or to other inspection/observation means (not shown). Then, control is returned to the initial screen.

According to one aspect of the third preferred embodiment, the entire surface of each wafer can be inspected using a SEM image thereof to detect true pattern defects 57 only. Thus, the user can identify the true pattern defects 57 with ease.

Further, according to another aspect of the third preferred embodiment, in cases where rough patterning is used to form a redundant power wiring layer or a pattern edge, the degree of roughness in patterning can be examined by means of display changeover.

Still further, according to another aspect of the third preferred embodiment, an image processing condition can be set so that false defects identified under actual inspection conditions will not be detected. It is therefore possible for the user to specify a threshold properly just as required.

Furthermore, according to another aspect of the third preferred embodiment, the image processing condition 201 is adjustable without completely deleting data of pattern defects 11 in the image processing region 200. Therefore, the user can adjust the image processing condition 201 so that false defect detection will be prevented as require d while possible defects remain inspectable.

As set forth hereinabove, and according to the present invention, the user can set up a non-inspection region that is effective for a device having a complex, large pattern area to be inspected, such as a wafer. Further, in cases where a considerable difference is found in comparative inspection of detected images, even if the difference is not actually a defect, the present invention makes it possible to avoid false defect detection while carrying out detection of minuscule defects.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which care within the meaning and range of equivalency of the claims are therefore intended to be embraced therein.

What is claimed is:

1. A pattern inspection apparatus comprising:
   an image detecting part for detecting a digital image of an object substrate;
   a display having a screen on which the digital image of the object substrate and/or a distribution of defect candidates in a map form are displayable;
   an input device for inputting information of a non-inspection region to be masked on the object substrate by defining a region on the screen on which said distribution of defect candidates is displayed in a map form;
   a memory part for storing coordinate data, pattern data or feature quantity data of the non-inspection region to be masked on the object substrate inputted on the screen by the input device; and
   a defect judging part in which the digital image detected by the image detecting part is examined in a state that a region matching with a condition stored in the memory part is masked and a defect is detected in a region other than said masked region.

2. A pattern inspection apparatus comprising:
   image detecting means for obtaining a digital image of an object substrate on which a pattern is formed, through microscopic observation thereof;
   a display having a screen on which the digital image of the object substrate is displayable;
   an input device for user-inputting information of a user-originated region to be masked on the object substrate;
   defect detecting means for detecting defects of the pattern formed on said object substrate by comparing the digital image attained by the image detecting means with a reference image; and
   output means for outputting data regarding the defects detected by the defect detecting means by masking and excluding defects from the user-originated region matching with the information inputted by the input device.

3. A pattern inspection apparatus as claimed in claim 2, wherein the user-originated region is set up using the digital image obtained by the image detecting means through microscopic observation of the object substrate by the input device.

4. A pattern inspection apparatus as claimed in claim 1, wherein said image detecting part includes an electron beam generator which emits an electron beam and a detector which detects a secondary electron emanated from said object substrate by the irradiation of said electron beam, to detect the image of said object substrate.

5. A pattern inspection apparatus as claimed in claim 1, wherein said image detecting part includes a light source which illuminates said object substrate with light, and a detector which detects light from the object substrate illuminated by said light source, to detect the image of said object substrate.

6. A pattern inspection apparatus as claimed in claim 2, wherein said image detecting part includes an electron beam generator which emits an electron beam and a detector which detects a secondary electron emanated from said object substrate by the irradiation of said electron beam to detect the image of said object substrate.

7. A pattern inspection apparatus as claimed in claim 2, wherein said image detecting part includes a light source which illuminates said object substrate with light, and a detector which detects light from the object substrate illuminated by said light source, to detect the image of said object substrate.

8. A pattern inspection apparatus as claimed in claim 1, wherein the inputting is effected by a human user manually designating the non-inspection region on the display screen.

9. A pattern inspection apparatus as claimed in claim 2, wherein the user-inputting is effected by a human user manually designating the user-originated region to be masked, on the display screen.

10. A pattern inspection apparatus comprising:
 an image detecting part for detecting a digital image of an object substrate;
 a display having a screen on which the digital image of the object substrate and/or a distribution of defect candidates in a map form are displayable;
 an input device for user-inputting information of a user-originated non-inspection region to be masked on the object substrate by defining a region on the screen on which said distribution of defect candidates is displayed in a map form;
 a memory part for storing coordinate data, pattern data or feature quantity data of the user-originated non-inspection region to be masked on the object substrate user-inputted on the screen by the input device; and
 a defect judging part in which the digital image detected by the image detecting part is examined in a state that the user-originated non-inspection region matching with a condition stored in the memory part is masked and a defect is detected in a region other than the user-originated non-inspection region.

11. A pattern inspection apparatus as claimed in claim 10, wherein said image detecting part includes an electron beam generator which emits an electron beam and a detector which detects a secondary electron emanated from said object substrate by the irradiation of said electron beam, to detect the image of said object substrate.

12. A pattern inspection apparatus as claimed in claim 10, wherein said image detecting part includes a light source which illuminates said object substrate with light, and a detector which detects light from the object substrate illuminated by said light source, to detect the image of said object substrate.

13. A pattern inspection apparatus as claimed in claim 10, wherein the user-inputting is effected by a human user manually designating the user-originated non-inspection region on the display screen.

* * * * *